(12) United States Patent
Bourrie et al.

(10) Patent No.: US 7,390,818 B2
(45) Date of Patent: Jun. 24, 2008

(54) PYRIDOINDOLONE DERIVATIVES SUBSTITUTED IN THE 3-POSITION BY A PHENYL, THEIR PREPARATION AND THEIR APPLICATION IN THERAPEUTICS

(75) Inventors: Bernard Bourrie, Saint-Gely-du-Fesc (FR); Pierre Casellas, Montpellier (FR); Paola Ciapetti, Altorf (FR); Jean-Marie Derocq, Murviel les Montpellier (FR); Samir Jegham, Montferrier-sur-Lez (FR); Yvette Muneaux, Les Matelles (FR); Camille-Georges Wermuth, Strasbourg (FR)

(73) Assignee: Sanofi-Aventis, Paris (FR)

( * ) Notice: Subject to any disclaimer, the term of this patent is extended or adjusted under 35 U.S.C. 154(b) by 226 days.

(21) Appl. No.: 11/109,068

(22) Filed: Apr. 19, 2005

(65) Prior Publication Data

US 2005/0288318 A1 Dec. 29, 2005

Related U.S. Application Data

(63) Continuation of application No. PCT/FR03/03110, filed on Oct. 21, 2003.

(30) Foreign Application Priority Data

Oct. 23, 2002 (FR) .................................. 02 13264

(51) Int. Cl.
 *A61K 31/437* (2006.01)
 *C07D 471/04* (2006.01)
(52) U.S. Cl. .............................. 514/292; 546/81; 546/84
(58) Field of Classification Search .................. 546/81, 546/84; 514/292
See application file for complete search history.

(56) References Cited

U.S. PATENT DOCUMENTS

| | | | |
|---|---|---|---|
| 4,263,304 | A | 4/1981 | Ishizumi et al. |
| 4,835,160 | A | 5/1989 | Bisagni et al. |
| 5,880,126 | A | 3/1999 | Skuballa et al. |
| 6,503,888 | B1 | 1/2003 | Kaplitt et al. |
| 2002/0156016 | A1 | 10/2002 | Minuk |
| 2004/0122027 | A1 | 6/2004 | Bourrie et al. |
| 2004/0122036 | A1 | 6/2004 | Bourrie et al. |

FOREIGN PATENT DOCUMENTS

| | | |
|---|---|---|
| FR | 2 003 999 | 11/1969 |
| FR | 2 765 581 | 1/1999 |
| FR | 2 765 582 | 1/1999 |
| SU | 833971 | 5/1981 |
| WO | WO 99/51597 | 10/1999 |
| WO | WO 01/09129 | 2/2001 |
| WO | WO 02/087574 | 11/2002 |
| WO | WO 02/087575 | 11/2002 |
| WO | WO 2004/037821 | 5/2004 |
| WO | WO 2005/108398 | 11/2005 |
| WO | WO 2007/045758 | 4/2007 |

OTHER PUBLICATIONS

F. Zaragoza Dorwald et al , Side Reactions in Organic Synthesis. 2005.*
Side reactions. Chapter 1 , pp. 8 and 9. , 2006.*
U.S. Appl. No. 11/109,121, Bourrie et al.
Furihata, C., et al., In Vivo Short-Term Assays For Tumor Initiation ANd Promotion In The Grandular Stomach Of Fischer Rats, Mutation Research, (1995), vol. 339, No. 1, pp. 15-35.
Furihata, C., et al., Unscheduled DNA Synthesis in Rat Stomach-Short-Term Assay Of Potential Stomach Carcinogens, Banbury Report,.(1982), vol. 13, pp. 123-135.
Golovko, T., et al., A New Approach To The Synthesis Of Functionally-Substituted Pyrido 2, 3-D Indoles, Mendeleev Communications, (1995), vol. 6, pp. 226-227.
Molina, P., et al., Annulation Of Pyridine To Indole By A Tandem Aza-Wittig/Electrocyclization Strategy: Synthesis Of Pyrido 2, 3-B Indoles, Synthesis, (1989), vol. 11, pp. 878-880.
Froissant et al., Derwent Patent Abstract No. 199909 (2003) (abstract of FR 2 765 581).
Goldman M.D., et al., Cecil, Textbook of Medicine, 21st edition, vol. 1, published 2000 by W.B. Saunders Co. (PA), pp. 1060-1074.
Abstract No. 1982-25808e (XP-002184731, DW 198213) (1982).
Derwent Patent Abstract No. 196800 (2003).
U.S. Appl. No. 11/582,769, filed Oct. 18, 2006, Bourrie.
Maribout Benoit et al, Derwent Patent Abstract No. 199909 (2003), (Abstract of FR 2 765 582).
Goodman & Gilman, Section X. Chemotherapy of Neoplastic Diseases, Goodman & Gilman's the Pharmacological Basis of Therapeutics, 9th Ed., (1996) pp. 1225-1232 and pp. 1269-1271.
Nicholson-Guthrie et al, Urine GABA Levels in Ovarian Cancer Patients: elevated GABA in malignancy, Cancer Letters, vol. 162, Issue 1, (2001), pp. 27-30.

* cited by examiner

*Primary Examiner*—Rita J Desai
(74) *Attorney, Agent, or Firm*—Kelly L. Bender

(57) ABSTRACT

The present invention relates to pyridoindolone derivatives substituted in the 3-position by a phenyl of general formula (I):

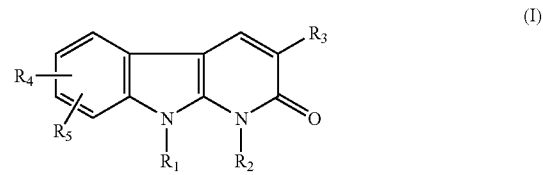

to processes for preparing the same and to their use in therapeutics.

10 Claims, No Drawings

PYRIDOINDOLONE DERIVATIVES SUBSTITUTED IN THE 3-POSITION BY A PHENYL, THEIR PREPARATION AND THEIR APPLICATION IN THERAPEUTICS

This application is a continuation of International Application PCT/FR2003/003110, filed Oct. 21, 2003.

The present invention relates to pyridoindolone derivatives substituted in the 3-position by a phenyl, to their preparation and to their application in therapeutics.

French Patent No. 97 08409 discloses compounds of formula:

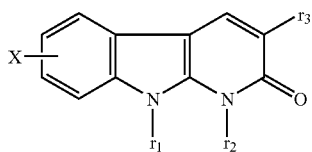

(A)

in which:
x represents a hydrogen or chlorine atom or a methyl or methoxy group;
$r_1$ represents a hydrogen atom or a methyl or ethyl group;
$r_2$ represents a methyl or ethyl group; or else
$r_1$ and $r_2$ together form a $(CH_2)_3$ group;
$r_3$ represents either, on the one hand, a phenyl group optionally substituted by a halogen atom or a methyl or methoxy group or, on the other hand, a thienyl group.

In the description of this patent, it is mentioned that the compounds of formula (A), which have an affinity for the omega modulatory sites associated with $GABA_A$ receptors, can be used in the treatment of conditions related to disorders of GABAergic transmission associated with $GABA_A$ receptor subtypes, such as anxiety, sleep disorders, epilepsy, and the like.

A subject-matter of the present invention is compounds having an anticancer activity corresponding to the formula:

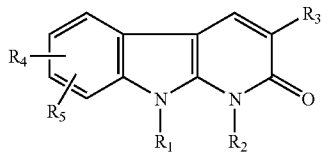

(I)

in which:
$R_1$ represents a hydrogen atom, a $(C_1-C_4)$alkyl group or a $(CH_2)_n$OH, $(CH_2)_n$—O-tetrahydropyran-2-yl, $(CH_2)_n$NR'$_6$R'$_7$, $(CH_2)_n$CN, $(CH_2)_n$CO$_2$(C$_1$-C$_4$)alk or $(CH_2)_n$CONR$_6$R$_7$ group;
$R_2$ represents a hydrogen atom or a $(C_1-C_4)$alkyl group;
or $R_1$ and $R_2$ together form a $(CH_2)_3$ group;
$R_3$ represents a phenyl monosubstituted by a hydroxyl, hydroxymethyl, carboxyl, $(C_1-C_4)$alkanoyl, azido, $(C_1-C_4)$alkoxycarbonyl, hydroxyiminomethyl, $(C_1-C_4)$alkylsulphonyl, trifluoromethyl, thiol, $(C_1-C_4)$alkylthio or cyano group or by a $(CH_2)_m$NR'$_7$R$_{10}$, CONR$_6$R$_8$ or O(CH$_2$)$_n$R$_9$ group; a phenyl substituted by 2 to 5 identical or different substituents chosen from a halogen atom, a $(C_1-C_4)$alkyl, trifluoromethyl, hydroxyl, hydroxymethyl, $(C_1-C_4)$alkoxy, carboxyl, $(C_1-C_4)$alkanoyl, azido, $(C_1-C_4)$alkoxycarbonyl, hydroxyiminomethyl, thiol, $(C_1-C_4)$alkylthio or $(C_1-C_4)$alkylsulphonyl group, or a phenyl or cyano, or by a $(CH_2)_m$NR'$_7$R$_{10}$, CONR$_6$R$_8$ or O(CH$_2$)$_n$R$_9$ group; or $R_3$ represents a benzodioxolyl group which is unsubstituted or substituted on the phenyl by a halogen atom;
$R_4$ and $R_5$ are identical or different and each independently represent a hydrogen or halogen atom or a hydroxyl, $(C_1-C_4)$alkyl, trifluoromethyl, phenyl, cyano, $(C_1-C_4)$alkoxy, $(C_1-C_4)$alkoxycarbonyl or $(C_1-C_4)$alkylsulphonyl group or an O—$(CH_2)_n$NR$_6$R$_7$ or $(CH_2)_n$NR$_6$R$_7$ group;
$R_6$ represents hydrogen or a $(C_1-C_4)$alkyl group;
$R_7$ represents hydrogen or a $(C_1-C_4)$alkyl group;
or $R_6$ and $R_7$, together with the nitrogen atom to which they are bonded, form a heterocyclic radical chosen from: piperidyl, morpholinyl, pyrrolidinyl, piperazinyl or 4-methylpiperazin-1-yl;
R'$_6$ represents hydrogen or a $(C_1-C_4)$alkyl group;
R'$_7$ represents hydrogen or a $(C_1-C_4)$alkyl group;
or R'$_6$ and R'$_7$, together with the nitrogen atom to which they are bonded, form a heterocyclic radical chosen from morpholinyl or pyrrolidinyl;
$R_8$ represents hydrogen, a $(C_1-C_4)$alkyl group or a —$(CH_2)_n$NR$_6$R$_7$ group;
or $R_6$ and $R_8$, together with the nitrogen atom to which they are bonded, form a heterocyclic radical chosen from: piperidyl, morpholinyl, pyrrolidinyl, piperazinyl or 4-methylpiperazin-1-yl;
$R_9$ represents a phenyl radical or an amino, morpholin-4-yl, cyano or $(C_1-C_4)$alkoxycarbonyl group;
$R_{10}$ represents R'$_6$ or a phenyl, pyridyl or pyrimidinyl group or a $(CH_2)_n$NR'$_6$R'$_7$ group;
or R'$_7$ and $R_{10}$, together with the nitrogen atom to which they are bonded, form a heterocyclic radical chosen from piperazinyl or 4-methylpiperazin-1-yl;
n represents 1, 2 or 3;
m represents 0 or 1;
Alk represents an alkyl.

The compounds of formula (I) can exist in the form of bases or of addition salts with acids. Such addition salts form part of the invention.

These salts are advantageously prepared with pharmaceutically acceptable acids but the salts of other useful acids, for example for the purification or isolation of the compounds of formula (I), also form part of the invention.

The compounds of formula (I) can also exist in the form of hydrates or of solvates, namely in the form of associations or combinations with one or more water molecules or with a solvent. Such hydrates and solvates also form part of the invention.

In the context of the present invention:
a halogen atom is understood to mean: a fluorine, a chlorine, a bromine or an iodine;
a $(C_1-C_4)$alkyl group is understood to mean: a saturated, linear or branched, aliphatic group comprising 1 to 4 carbon atoms. Mention may be made, by way of example, of the methyl, ethyl, propyl, butyl, isobutyl and tert-butyl groups;
a $(C_1-C_4)$alkoxy group is understood to mean: an O-alkyl radical where the alkyl group is as defined above.

A subject-matter of the present invention is very particularly compounds of formula (I) in which:
$R_1$ represents a hydrogen atom, a $(C_1-C_4)$alkyl group or a $(CH_2)_n$CO$_2$(C$_1$-C$_4$)alk or $(CH_2)_n$CONR$_6$R$_7$ group;
$R_2$ represents a hydrogen atom or a $(C_1-C_4)$alkyl group;

$R_3$ represents a phenyl monosubstituted by a hydroxyl, hydroxymethyl, carboxyl, $(C_1-C_4)$alkoxycarbonyl, hydroxyiminomethyl, $(C_1-C_4)$alkylsulphonyl, trifluoromethyl, thiol, $(C_1-C_4)$alkylthio or cyano group or by a $(CH_2)_m NR_6R_7$ or $CONR_6R_8$ group; a phenyl substituted by 2 to 5 identical or different substituents chosen from a halogen atom or a $(C_1-C_4)$alkyl, trifluoromethyl, hydroxyl, hydroxymethyl, $(C_1-C_4)$alkoxy, carboxyl, $(C_1-C_4)$alkoxycarbonyl, hydroxyiminomethyl, thiol, $(C_1-C_4)$alkylthio, $(C_1-C_4)$alkylsulphonyl or cyano group or by a $(CH_2)_m NR_6R_7$ or $CONR_6R_8$ group; or $R_3$ represents a benzodioxolyl group;

$R_4$ and $R_5$ are identical or different and each independently represent a hydrogen or halogen atom or a hydroxyl, $(C_1-C_4)$alkyl, trifluoromethyl, cyano, $(C_1-C_4)$alkoxy or $(C_1-C_4)$alkoxycarbonyl group or an $O—(CH_2)_n NR_6R_7$ group;

$R_6$ represents hydrogen or a $(C_1-C_4)$alkyl group;

$R_7$ represents hydrogen or a $(C_1-C_4)$alkyl group;

or $R_6$ and $R_7$, together with the nitrogen atom to which they are bonded, form a heterocyclic radical chosen from: piperidyl, morpholinyl, pyrrolidinyl, piperazinyl or 4-methylpiperazin-1-yl;

$R_8$ represents hydrogen, a $(C_1-C_4)$alkyl group or a $—(CH_2)_n NR_6R_7$ group;

or $R_6$ and $R_8$, together with the nitrogen atom to which they are bonded, form a heterocyclic radical chosen from: piperidyl, morpholinyl, pyrrolidinyl, piperazinyl or 4-methylpiperazin-1-yl;

n represents 1, 2 or 3;

m represents 0 or 1;

Alk represents an alkyl.

Mention may be made, among the compounds of formula (I) which are subject-matters of the invention, of the preferred compounds which are defined as follows:

$R_1$ represents a hydrogen atom or a methyl, cyanomethyl, $(C_1-C_4)$ alkoxycarbonylmethyl, aminomethyl, aminoethyl, aminopropyl or pyrrolidinoethyl group;

and/or $R_2$ represents a methyl group;

and/or $R_1$ and $R_2$ together form a $(CH_2)_3$ group;

and/or $R_3$ represents a phenyl monosubstituted by a hydroxyl, $(C_1-C_4)$alkoxycarbonyl, methylsulphonyl, trifluoromethyl, methylthio, cyanomethoxy, aminoethoxy, acetyl, hydroxymethyl, cyano, amino, azido, aminomethyl or hydroxyiminomethyl group or a $(CH_2)_m NR'_7R_{10}$ group in which $R'_7$ represents a hydrogen atom or a methyl, $R_{10}$ represents a hydrogen atom or a phenyl, pyridyl or pyrimidinyl group or $R'_7$ and $R_{10}$, together with the nitrogen atom to which they are bonded, form a piperazin-1-yl or 4-methylpiperazin-1-yl group, and m represents zero or one; or $R_3$ represents a phenyl substituted by 2 to 3 identical or different substituents chosen from a halogen atom, a methyl, methoxy, methylthio, trifluoromethyl, hydroxyl, $(C_1-C_4)$ alkoxycarbonyl, methylsulphonyl, cyanomethoxy, aminoethoxy, acetyl, hydroxymethyl, cyano, amino, azido, aminomethyl or hydroxyiminomethyl group or a $(CH_2)_m NR'_7R_{10}$ group in which $R'_7$ represents a hydrogen atom or a methyl, $R_{10}$ represents a hydrogen atom or a phenyl, pyridyl or pyrimidinyl group or $R'_7$ and $R_{10}$, together with the nitrogen atom to which they are bonded, form a piperazin-1-yl or 4-methylpiperazin-1-yl group, and m represents zero or one; or $R_3$ represents a benzodioxolyl group which is unsubstituted or substituted on the phenyl by a halogen atom;

and/or $R_4$ represents a halogen atom or a methyl, methoxy or $(C_1-C_4)$alkoxycarbonyl group;

and/or $R_5$ represents a hydrogen atom or a methyl group.

Preference is very particularly given to the following compounds:

3-(2,4-dimethoxyphenyl)-1,9-dimethyl-2-oxo-2,9-dihydro-1H-pyrido[2,3-b]indole-6-carboxylic acid;

3-(2,4-dimethoxyphenyl)-1,6-dimethyl-1,9-dihydro-2H-pyrido[2,3-b]indol-2-one;

3-(3-hydroxymethylphenyl)-1,6-dimethyl-1,9-dihydro-2H-pyrido[2,3-b]indol-2-one;

3-(2,4-dichlorophenyl)-1,6-dimethyl-1,9-dihydro-2H-pyrido[2,3-b]indol-2-one;

3-(1,6-dimethyl-2-oxo-2,9-dihydro-1H-pyrido[2,3-b]-indol-3-yl)benzonitrile;

3-(4-aminophenyl)-1,6-dimethyl-1,9-dihydro-2H-pyrido[2,3-b]indol-2-one;

3-(6-chloro-1,3-benzodioxol-5-yl)-1,6-dimethyl-1,9-dihydro-2H-pyrido[2,3-b]indol-2-one;

1,6-dimethyl-1,9-dihydro-3-(phenylaminophenyl)-2H-pyrido[2,3-b]indol-2-one;

6-bromo-3-(3,5-dimethylphenyl)-1-methyl-1,9-dihydro-2H-pyrido[2,3-b]indol-2-one;

1,6-dimethyl-3-(3-(trifluoromethyl)phenyl)-1,9-dihydro-2H-pyrido[2,3-b]indol-2-one;

1,6-dimethyl-3-(3-(pyridin-2-ylamino)phenyl)-1,9-dihydro-2H-pyrido[2,3-b]indol-2-one;

1,6-dimethyl-3-(3-(pyrimidin-2-ylamino)phenyl)-1,9-dihydro-2H-pyrido[2,3-b]indol-2-one;

3-(3-acetylphenyl)-1,6-dimethyl-1,9-dihydro-2H-pyrido[2,3-b]indol-2-one;

2-(2,4-dichlorophenyl)-9-methyl-5,6-dihydro-3H,4H-3a,6a-diazafluoranthen-3-one;

methyl 9-(cyanomethyl)-3-(2,4-dichlorophenyl)-2-oxo-2,9-dihydro-1H-pyrido[2,3-b]indole-6-carboxylate;

and their addition salts, their solvates and their hydrates.

In that which follows, protective group Gp or G'p is understood to mean a group which makes it possible, first, to protect a reactive functional group, such as a hydroxyl or an amine, during a synthesis and, secondly, to regenerate the intact reactive functional group at the end of the synthesis. Examples of protective groups and methods for protection and deprotection are given in "Protective Groups in Organic Synthesis", Green et al., $2^{nd}$ Edition (John Wiley & Sons Inc., New York).

The term "leaving group" is understood to mean, in that which follows, a group which can be easily cleaved from a molecule by splitting a heterolytic bond, with departure of an electron pair. This group can thus be easily replaced by another group during a substitution reaction, for example. Such leaving groups are, for example, halogens or an activated hydroxyl group, such as a mesyl, tosyl, triflate, acetyl, and the like. Examples of leaving groups and references for their preparation are given in "Advances in Organic Chemistry", J. March, $3^{rd}$ Edition, Wiley Interscience, p. 310-316.

In accordance with the invention, the compounds of general formula (I) can be prepared according to the following process.

This process is characterized in that: a 2-aminoindole of formula:

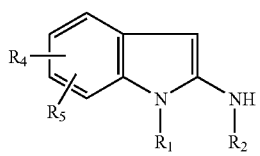

in which $R_1$, $R_2$, $R_4$ and $R_5$ are as defined for a compound of formula (I), is reacted with an ester of formula:

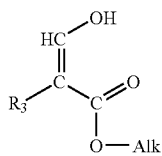

in which $R_3$ is as defined for a compound of formula (I) and Alk represents a $C_1$-$C_4$ alkyl.

The reaction is carried out in a polar and preferably basic solvent, for example in pyridine, at a temperature of between ambient temperature and the reflux temperature of the solvent.

Generally, it is also possible to prepare, according to the process of the invention, a compound of formula:

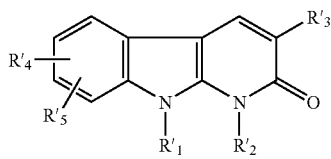

in which the $R'_1$, $R'_2$, $R'_3$, $R'_4$ and $R'_5$ substituents are precursors of the $R_1$, $R_2$, $R_3$, $R_4$ and $R_5$ substituents as defined for a compound of formula (I), and then, by using methods known to a person skilled in the art, to convert these substituents in order to obtain the $R_1$, $R_2$, $R_3$, $R_4$ and $R_5$ substituents desired for the compound of formula (I).

A compound of formula (I) in which $R_1$ and/or $R_2$ is an alkyl group is prepared from a compound of formula (I) in which $R_1$ or $R_2$ is hydrogen by the action of an alkyl iodide in the presence of NaH.

The compounds of formula (I) in which the $R_1$ substituent is a —$(CH_2)_nCO_2(C_1$-$C_4)$Alk or —$(CH_2)_nCONR_6R_7$ group are prepared from the corresponding compounds of formula (I)' in which $R_1$=H and $R_2$, $R_3$, $R_4$ and $R_5$ have the same values.

For example, a compound of formula (I) in which $R_1$=H can be substituted by a $(CH_2)_2CN$ group by reacting with a compound of formula $Br(CH_2)_nCN$ in the presence of sodium hydride.

Furthermore, in order to prepare a compound of formula (I) in which $R_1$ represents a $(CH_2)_nNR'_6R'_7$ group, a brominated compound of formula $Br(CH_2)_nNR'_6R'_7$ can be reacted with a compound of formula (I) in which $R_1$=H.

More generally, in order to prepare a compound of formula (I) in which $R_1$ represents a $(CH_2)_nNR'_6R'_7$ group, a compound of formula $X(CH_2)_nNGp$ in which X represents a leaving group, such as a bromine atom or a mesyl or tosyl group, for example, and Gp represents a protective group for the nitrogen can be reacted with a compound of formula (I) in which $R_1$=H; after deprotection of the nitrogen, it is possible, if appropriate, to alkylate the amine formed by using methods known to a person skilled in the art.

To prepare a compound of formula (I) in which $R_1$ represents a $(CH_2)_nOH$ group, a compound of formula $X(CH_2)_nO$-G'p in which X is a leaving group and G'p is a protective group for the oxygen can be reacted with a compound of formula (I) in which $R_1$=H and then the compound thus obtained can be treated to remove the protective group by methods known to a person skilled in the art.

To prepare a compound of formula (I) in which the $R_3$ and/or $R_4$ and/or $R_5$ substituents comprise a hydroxymethyl, hydroxyiminomethyl, alkylaminomethyl or dialkylaminomethyl group, the corresponding compound of formula (I) carrying an $R_3$ and/or $R_4$ and/or $R_5$ substituent comprising a cyano group is converted by methods known to a person skilled in the art.

To prepare a compound of formula (I) in which the $R_3$ and/or $R_4$ and/or $R_5$ substituents comprise a hydroxyl group, it is possible to prepare first an analogous compound of formula (I) in which the $R_3$ and/or $R_4$ and/or $R_5$ substituents comprise a protected hydroxyl group and then, in a subsequent stage, to convert this group to a hydroxyl by methods known to a person skilled in the art. Use may be made, as protective group for the hydroxyl, of a benzyl, a benzoyl or a $(C_1$-$C_4)$alkyl, for example.

The compounds of formula (I) in which $R_4$ and/or $R_5$ represent a Br atom or the substituent(s) on the $R_3$ phenyl group represent(s) one (or several) bromine atom(s) can be used as precursors for preparing other compounds according to the invention, for example compounds carrying amine substituents, such as $(CH_2)_nNR_6R_7$ or $(CH_2)_mNR'_7R_{10}$, by using reactions known to a person skilled in the art.

Compounds carrying a brominated substituent are also of use for the preparation of compounds carrying an alkoxycarbonyl substituent.

The aminoindoles of formula (II) can be prepared by methods such as those described in Khim. Geterosikl. Soedin., 1973, 12, 647-652 and in J. Heterocycl. Chem., 1975, 12, 135-138.

Some 2-aminoindole derivatives of formula (II) are known and are described in Khim. Geterosikl. Soedin., 1973, 4, 511-515; Eur. J. Med. Chem. Chim. Ther., 1992, 27 (9), 908-918; Chem. Heterocycl. Compd. (Engl. Transl.), 1970, 6, 338-343; Tetrahedron, 1971, 27, 775-785; Pharm. Chem. J. (Engl. Transl.), 1990, 24 (11), 810-812; Tetrahedron Lett., 1996, 37 (28), 4931-4932.

Some esters of formula (III) are known and can be prepared by methods such as those described in J. Org. Chem., 1984, 49 (22), 4287-4290; J. Am. Chem. Soc., 1974, 96 (7), 2121; Tetrahedron, 1970, 26 (2), 715-719; Synth. Commun., 2000, 30 (8), 1401-1411; Zhongguo Yaowu Huaxue Zazhi, 2000, 10 (1), 9-12, 25; JP 19 680 131, EP 260 832, EP 178 826, WO 97-46 577, DE 3 221 915.

The compounds according to the invention can also be prepared by a process characterized in that: an aminoindole of formula:

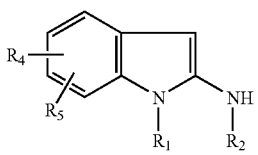

in which $R_1$, $R_2$, $R_4$ and $R_5$ are as defined for a compound of formula (I), is reacted with an ester of formula:

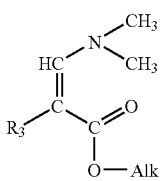

in which $R_3$ is as defined for a compound of formula (I) and Alk represents a $C_1$-$C_4$ alkyl.

The reaction is carried out in a protic and polar solvent, preferably in an acidic medium, at a temperature of between ambient temperature and the reflux temperature of the solvent.

The compound of formula (IV) is prepared using dimethoxy-N,N-dimethylmethanamine (V) by a method similar to that described in J. Org. Chem., 1982, 47, 2846-2851 or using Bredereck's reagent (tert-butoxybis(dimethylamino)methane) according to J. Org. Chem., 1982, 15, 2846-2851 and according to the following reaction scheme:

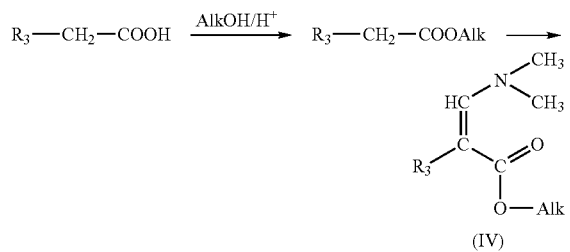

Unless otherwise indicated, the proton nuclear magnetic resonance (NMR) spectra are recorded in $d_6$-DMSO; the reference is placed in the $d_6$-DMSO, which lies at 2.50 ppm from the tetramethylsilane.

The signals observed by NMR spectroscopy are expressed thus: s: singlet; bs: broad singlet; d: doublet; sd: split doublet; t: triplet; st: split triplet; q: quartet; mt: multiplet.

The preparation of some compounds in accordance with the invention is described in the following examples. These examples are not limiting and serve only to illustrate the present invention. The numbers of the compounds in the examples refer to those given in the table below, in which the chemical structures and the physical properties of a few compounds according to the invention are illustrated.

In the preparations and examples which will follow, the following abbreviations are used:
TEA: triethylamine
DMA: dimethylacetamide
DMF: dimethylformamide
DBU: 1,8-diazabicyclo[5.4.0]undec-7-ene
LAH: $LiAlH_4$: lithium aluminium hydride
NMP: N-methylpyrrolidin-2-one
$LiN(TMS)_2$: lithium bis(trimethylsilyl)amide
DCM: dichloromethane
AcOEt: ethyl acetate
AcOH: acetic acid
NBS: N-bromosuccinimide
AIBN: 2,2'-azobisisobutyronitrile
Xant phos: 4,5-bis(diphenylphosphino)-9,9-dimethylxanthene
$Pd(dba)_3$: tris(dibenzylideneacetone)dipalladium
BOP: benzotriazol-1-yloxytris(dimethylamino)phosphonium hexafluorophosphate
MTBE: methyl tert-butyl ether
MiBK: methyl isobutyl ketone
Bredereck's reagent: tert-butoxybis(dimethylamino)methane
AT: ambient temperature Preparation of the Compounds of Formula (II)

The compounds of formula (II) can exist in two tautomeric forms:

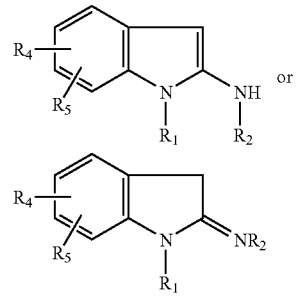

Preparation 1.1

N,1,5-Trimethyl-1H-indole-2-amine Hydrochloride

A) N'-(4-Methylphenyl)acetohydrazide 104.8 g of 1-(4-methylphenyl)hydrazine hydrochloride are suspended in 525 ml of isopropyl acetate, a solution of 104.8 g of potassium carbonate in 300 ml of water is added and then the mixture is stirred until the solid has disappeared. 77.4 g of acetic anhydride are added while maintaining the temperature below 20° C. and then the mixture is left stirring at 20° C. A precipitate is observed to form, which precipitate disappears when the mixture is heated at approximately 55-60° C. The organic phase is washed twice with 200 ml of water and is then cooled at 0-5° C. overnight. The product formed is recovered by filtration and is then washed twice with 100 ml of MTBE.

NMR $CDCl_3$ (300 MHz):2.02 ppm:s:3H; 2.29 ppm:s:3H; 6.14 ppm:d:1H; 6.73 ppm:d:2H; 7.03 ppm:d:2H; 7.72 ppm:s:1H.

B) N,N'-Dimethyl-N'-(4-methylphenyl)acetohydrazine 60 g of hydrazine from the preceding stage and 11.8 g of tetrabutylammonium bromide are suspended in 240 ml of toluene, and 292 g of 50% NaOH in water and then 155.6 g of methyl iodide are added. 83 g of sodium hydroxide pellets are then added and then the reaction medium is heated at 80° C. for 6 hours. The mixture is cooled to 30-35° C. and then 500 ml of water are added. The organic phase is washed three times with 100 ml of water. The organic phase is dried by azeotropic distillation of the water under reduced pressure.

NMR CDCl$_3$ (300 MHz):2.15 ppm:s:3H; 2.31 ppm:s:3H; 2.95 ppm:s:3H; 3.10 ppm:s:3H; 6.63 ppm:d:2H; 7.13 ppm:d: 2H.

C) N,1,5-Trimethyl-1H-indole-2-amine hydrochloride

The product obtained in the preceding stage is dissolved in toluene, 61.5 g of phosphorus oxychloride are added and the mixture is heated at 80° C. for 2 hours. 100 ml of ethyl acetate are added at 80° C. and then the medium is cooled to AT. The precipitate is filtered off and then washed twice with 50 ml of ethyl acetate, m.p.=222° C.

NMR d$_6$-DMSO (200 MHz):2.36 ppm:s:3H; 3.11 ppm:s: 3H; 3.49 ppm:s:3H; 4.29 ppm:s:1H; 7.25-7.35 ppm:unresolved peak:3H; 10.07 ppm:unresolved peak:1H.

Preparation 1.2

N,5-Dimethyl-1H-indole-2-amine dihydrochloride

A) N'-(4-Methylphenyl)acetohydrazide

Another process for the preparation of this compound is described below.

5 g of 1-(4-methylphenyl)hydrazine hydrochloride are dissolved in water and then triethylamine is added until the salt has been neutralized. Extraction is carried out with AcOEt and then the extract is evaporated to dryness. The precipitate formed is dissolved in 30 ml of ether and then a solution of 4.6 ml of acetic anhydride dissolved in 30 ml of ether is added dropwise. The mixture is stirred at 0° C. for 15 minutes and then the precipitate formed is filtered off to produce 3 g of the expected compound.

NMR CDCl$_3$ (300 MHz):2.02 ppm:s:3H; 2.29 ppm:s:3H; 6.14 ppm:d:1H; 6.73 ppm:d:2H; 7.03 ppm:d:2H; 7.72 ppm: s:1H.

B) N-Methyl-N'-(4-methylphenyl)acetohydrazide 0.8 g of 60% NaH is suspended in 30 ml of DMF. 3.2 g of hydrazine obtained in the preceding stage in 20 ml of DMF are added dropwise at 0° C. When gas evolution has ceased, 1.8 ml of methyl iodide are added and the mixture is stirred at AT for one hour. The mixture is poured onto a saturated NH$_4$Cl solution and then extraction is carried out with AcOEt. Washing is carried out several times with a saturated NaCl solution and then evaporation is carried out to dryness. The residue is purified by chromatography on a silica column eluted with an AcOEt/heptane mixture, (25/75; v/v) then (50/50; v/v), to produce 1.0 g of the expected compound in the form of a white powder.

NMR CDCl$_3$ (200 MHz):2.21 ppm:s:3H; 2.32 ppm:s:3H; 3.15 ppm:s:3H; 5.88 ppm:s:1H; 6.64 ppm:d:2H; 7.12 ppm:d: 2H.

C) N,5-Dimethyl-1H-indole-2-amine dihydrochloride 1.0 g of the compound from the preceding stage is dissolved in 20 ml of POCl$_3$ and then the mixture is heated at 100° C. for two hours. The reaction mixture is cooled and then ether is added. The precipitate formed is filtered off and is washed with ether to produce 1.3 g of the expected compound. NMR d$_6$-DMSO (300 MHz):2.31 ppm:s:3H; 3.05 ppm:s:3H; 4.14 ppm:s:2H; 7.07-7.23 ppm:unresolved peak: 3H; 10.51 ppm:s:1H; 12.37 ppm:d:1H.

Preparation 1.3

N,1-Dimethyl-5-methoxy-1H-indole-2-amine hydrochloride

A) N'-(4-Methoxyphenyl)acetohydrazide 10 g of 4-methoxyphenylhydrazine hydrochloride are dissolved in water and then triethylamine is added until the salt has been neutralized. Extraction is carried out with AcOEt and then the extract is evaporated to dryness to produce 8 g of precipitate composed of 4-methoxyphenyl-hydrazine. This compound is dissolved in 30 ml of ether and then a solution of 13 ml of acetic anhydride dissolved in 30 ml of ether is added dropwise. The mixture is stirred at 0° C. for 15 minutes and then the white precipitate formed is filtered off to produce 7.4 g of the expected compound.

NMR CDCl$_3$ (200 MHz):2.06 ppm:s:3H; 3.75 ppm:s:3H; 5.65 and 6.03 ppm:2s:2H; 6.6-6.9 ppm:unresolved peak:4H.

B) N,N'-Dimethyl-N'-(4-methoxyphenyl)acetohydrazide 4.3 g of 60% NaH are suspended in 30 ml of DMA. 7.4 g of the compound from the preceding stage, dissolved in 20 ml of DMA, are added dropwise. When gas evolution has ceased, 10.0 ml of iodomethane are added. The mixture is stirred at ambient temperature for one hour. It is poured onto a saturated NH$_4$Cl solution and then extraction is carried out with AcOEt. The organic phase is washed several times with a saturated NaCl solution and is then evaporated to dryness. The residue obtained is triturated in petroleum ether to produce 8.0 g of the expected compound in the form of an oil.

NMR CDCl$_3$ (200 MHz):2.19 ppm:s:3H; 2.93 ppm:s:3H; 3.08 ppm:s:3H; 3.80 ppm:s:3H; 6.68 ppm:d:2H; 6.89 ppm:d: 2H.

C) N,1-Dimethyl-5-methoxy-1H-indole-2-amine hydrochloride 8.0 g of the compound from the preceding stage are dissolved in 30 ml of POCl$_3$ and then the mixture is heated at 80° C. for 2 hours. The reaction mixture is cooled and then ether is added. The brown precipitate formed is filtered off and washed with ether to produce 5.3 g of the expected compound, m.p.=222° C.

NMR d$_6$-DMSO (300 MHz):3.06 ppm:s:3H; 3.48 ppm:s: 3H; 3.76 ppm:s:3H; 4.26 ppm:s:2H; 6.96-7.00 ppm:dd 1H; 7.14 ppm:d:1H; 7.24 ppm:d:1H; 10.08 ppm:s:1H.

Preparation 1.4

N,1-Dimethyl-5-chloro-1H-indole-2-amine hydrochloride

A) N'-(4-Chlorophenyl)acetohydrazide 12.5 g of 4-chlorophenylhydrazine hydrochloride are dissolved in 100 ml of water and then triethylamine is added until the salt has been neutralized. Extraction is carried out with AcOEt and then the extract is evaporated to dryness. The base is dissolved in 100 ml of ether, the solution is cooled to 0° C. and then 15 ml of acetic anhydride are added dropwise. The mixture is stirred at 0° C. for 15 minutes. The white precipitate formed is filtered off and is then washed with ether to produce 12.8 g of the expected compound in the form of a white powder.

NMR CDCl$_3$ (200 MHz):2.09 ppm:s:3H; 6.68-6.86 ppm: unresolved peak:2H; 7.12-7.30 ppm:unresolved peak:2H.

B) N,N'-Dimethyl-N'-(4-chlorophenyl)acetohydrazide 7.2 g of 60% NaH are suspended in 30 ml of DMA. 12.8 g of hydrazine from the preceding stage, dissolved in 50 ml of DMA, are added dropwise and the mixture is stirred at ambient temperature until gas evolution has ceased. 17 ml of iodomethane are added dropwise and the mixture is stirred at ambient temperature for one hour. The mixture is poured onto a saturated NH₄Cl solution and then extraction is carried out with AcOEt. The organic phase is washed with a saturated NaCl solution. The residue obtained is triturated with petroleum ether to produce 10 g of the expected compound in the crystalline form.

NMR CDCl₃ (200 MHz):2.10 ppm:s:3H; 2.95 ppm:s:3H; 3.10 ppm:s:3H; 6.62 ppm:d:2H; 7.24 ppm:d:2H.

C) N,1-Dimethyl-5-chloro-1H-indole-2-amine hydrochloride 10 g of the compound from the preceding stage are dissolved in 50 ml of POCl₃. The mixture is heated at reflux for two hours. The reaction medium is cooled, ether is added and then the product obtained is filtered off. The precipitate is washed several times with ether to produce 9.6 g of the expected compound in the form of a powder.

NMR d₆-DMSO (300 MHz):3.08 ppm:s:3H; 3.52 ppm:s: 3H; 4.31 ppm:s:2H; 7.34 ppm:d:1H; 7.48 ppm:d:1H; 7.60 ppm:s:1H; 10.61 ppm:s:1H.

Preparation 1.5

Methyl 1-methyl-2-(methylamino)-1H-indole-5-carboxylate

A) Methyl 4-(2-acetylhydrazino)benzoate 5.5 g of methyl 4-hydrazinobenzoate are dissolved in 38.2 ml of AcOH comprising 2.4 g of sodium acetate and the mixture is heated at 80° C. for 18 hours. The inorganic material is filtered off, the filtrate is then evaporated and the residue is taken up in the minimum amount of Et₂O. The mixture is filtered to produce 7.97 g of the expected compound.

B) Methyl 4-(2-acetyl-1,2-dimethylhydrazino)benzoate 2.95 g of 95% NaH are suspended in 90 ml of DMF, 8.135 g of the compound from the preceding stage, in solution in the minimum amount of DMF, are added dropwise and then, after a few minutes, 9.75 ml of methyl iodide are added dropwise. The mixture is stirred at AT for one hour. The medium is poured onto a saturated NH₄Cl solution and extraction is carried out with AcOEt. The organic phase is washed with NaCl, dried and evaporated to give 5.4 g of the expected compound.

C) Methyl 1-methyl-2-(methylamino)-1H-indole-5-carboxylate 5.4 g of the compound from the preceding stage and 62 ml of phosphorus oxychloride are mixed and the mixture is heated at 80° C. for two and a half hours. The medium is evaporated and the residue is taken up in AcOEt. The solid formed is filtered off, washed with AcOEt and dried to give 4 g of the expected compound.

NMR MeOD (250 MHz):3.2 ppm:s:3H; 3.6 ppm:s:3H; 3.9 ppm:s:3H; 7.3-7.4 ppm:unresolved peak:2H; 8.1-8.2 ppm: unresolved peak:2H.

The compounds of formula (II) collated in the table below are prepared by operating as described above:

TABLE 1

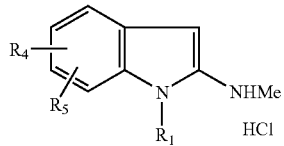

(II)

| Preparation | R₁ | R₄, R₅ | Characterization M.p. (° C.) or NMR |
|---|---|---|---|
| 1.6 | Me | H | 249° C. |
| 1.7 | Me | 7-OMe | 284° C. |
| 1.8 | Me | 4-OMe | 103° C. |
| 1.9 | Me | 6-OH | 103° C. |
| 1.10 | Me | 6-Me | |
| 1.11 | Me | 4,6-diMe | 134° C. |
| 1.12 | Me | 5-OMe | 222° C. |
| 1.13 | Me | 5-Cl | NMR |
| 1.14 | Me | 6-OMe | 103° C. |
| 1.15 | Me | 5-CN | 245° C. |
| 1.16 | Me | 5-phenyl | |

NMR 1.13 d₆-DMSO(300 MHz): 3.08 ppm: d: 3H; 3.52 ppm: s: 3H; 7.34 ppm: d: 1H; 7.48 ppm: d: 1H; 7.60 ppm: s: 1H; 10.61 ppm: s: 1H.

Preparation 1.17

Ethyl 2-(methylimino)indoline-5-carboxylate hydrochloride

A) Ethyl 4-hydrazinobenzoate 5.0 g of 4-hydrazinobenzoic acid are dissolved in 70 ml of ethanol and 3 ml of concentrated H₂SO₄. The mixture is heated at reflux for five hours, the ethanol is evaporated, the residue is then taken up in a saturated K₂CO₃ solution and then extraction is carried out with AcOEt. 5.9 g of the expected compound are obtained in the form of a powder.

NMR CDCl₃ (300 MHz):1.38 ppm:t:3H; 3.65 ppm:s:2H; 4.34 ppm:q:2H; 5.57 ppm:s:1H; 6.80 ppm:d:2H; 7.93 ppm: d:2H.

B) Ethyl 4-(N'-acetylhydrazino)benzoate 5.9 g of the compound from the preceding stage are dissolved in 50 ml of acetic acid, and 3.0 g of sodium acetate are added. The mixture is heated at 80° C. for 16 hours. The acetic acid is evaporated, the residue is taken up in water and then extraction is carried out with CH₂Cl₂. The organic phase is dried over MgSO₄ and is then evaporated to dryness. 4.2 g of powder are obtained.

NMR CDCl₃ (300 MHz):1.36 ppm:t:3H; 2.04 ppm:s:3H; 4.32 ppm:q:2H; 6.63 ppm:s:1H; 6.73 ppm:d (J=8.8):2H; 7.88 ppm:d:2H; 8.00 ppm:s:1H.

C) Ethyl 4-(N'-acetyl-N'-methylhydrazino)benzoate 0.72 g of 60% NaH is suspended in 20 ml of DMF. The mixture is cooled to 0° C. and then 4.0 g of the compound from the preceding stage, dissolved in 20 ml of DMA, are added. The mixture is stirred at 0° C. for 15 minutes, then 1.7 ml of iodomethane are added and the mixture is stirred at 0° C. for 30 minutes. It is poured onto a saturated NH₄Cl solution and extracted with AcOEt. The organic phase is washed with a saturated NaCl solution, dried over MgSO₄ and then adsorbed on silica. Purification is carried out by chromatography on a silica column eluted with an AcOEt/petroleum ether (v/v; 50/50) mixture. 1.8 g of oil are obtained.

NMR CDCl₃ (300 MHz):1.38 ppm:t:3H; 2.15 ppm:s:3H; 3.17 ppm:s:3H; 4.35 ppm:q (J=7.1):2H; 6.10 ppm:s:1H; 6.71 ppm:d (J=8.8):2H; 7.99 ppm:d:2H.

D) Ethyl 2-(methylimino)indoline-5-carboxylate hydrochloride 1.5 g of the compound from the preceding stage are dissolved in 10 ml of $POCl_3$. The mixture is heated at 80° C. for two hours. The reaction medium is cooled, ether is added and the precipitate formed is triturated and filtered off. It is washed with ether. 1.4 g of powder are obtained.

NMR $CDCl_3$ (300 MHz):1.31 ppm:t (J=7.1):3H; 3.07 ppm:d (J=4.7):3H; 4.25 ppm:s:2H; 4.31 ppm:q:2H; 7.58 ppm:d (J=8.8):1H; 7.99 ppm:unresolved peak: 2H; 10.97 ppm:s:1H; 12.81 ppm:s:1H.

Preparation 1.18

5-Bromo-N-methyl-1H-indole-2-amine hydrochloride

A) N'-(4-Bromophenyl)formohydrazide 10.0 g of 4-bromophenylhydrazine hydrochloride are dissolved in 30 ml of water. 6.2 g of $K_2CO_3$ and 36 ml of methyl formate are added and then the mixture is heated at reflux for one hour and then at ambient temperature for 12 hours. The precipitate formed is filtered off and washed with an isopropanol/petroleum ether (v/v; 50/50) mixture. 10.5 g of the expected product are obtained.

NMR $CDCl_3$ (300 MHz):6.73-6.77 ppm:unresolved peak: 2H; 7.34-7.41 ppm:unresolved peak:2H; 8.33 ppm:unresolved peak:1H.

B) N'-(4-Bromophenyl)-N-methylacetohydrazide

A solution of 80 ml of LAH in THF is heated to reflux. 10.5 g of the compound from the preceding stage, in suspension in 60 ml of THF, are added. The mixture is heated at reflux for 15 hours. The reaction medium is cooled and then 2.3 ml of water, then 9.0 ml of 1N NaOH and then again 10 ml of $H_2O$ are added dropwise. The salts are filtered off through Celite®, washing is carried out with AcOEt and then evaporation to dryness is carried out. The residue is taken up in 80 ml of AcOEt, then 17 g of $K_2CO_3$, dissolved in 80 ml of water, are added, followed by 4.0 ml of acetic anhydride. The mixture is stirred at ambient temperature for one hour. The two phases are separated and the organic phase is dried over $MgSO_4$ and then evaporated to dryness. Petroleum ether is added and then the crystals formed are filtered off. 9.0 g of the expected product are obtained.

NMR $CDCl_3$ (300 MHz):2.15 ppm:s:3H; 3.13 ppm:s:3H; 6.57-6.62 ppm:unresolved peak:2H; 7.32-7.40 ppm:unresolved peak:2H.

C) 5-Bromo-N-methyl-1H-indole-2-amine hydrochloride 9.0 g of hydrazine obtained in the preceding stage are dissolved in 50 ml of $POCl_3$ and then the mixture is heated at 80° C. for two hours. The reaction mixture is cooled and then ether is added. The precipitate formed is filtered off and washed with ether. 8.2 g of powder are obtained.

NMR $CDCl_3$ (300 MHz):4.31 ppm:s:3H; 7.14-7.87 ppm: unresolved peak:4H; 10.70 ppm:unresolved peak:1H; 12.62 ppm:s:1H.

Preparation 1.19

8-Methyl-1,2,3,4-tetrahydropyrimido[1,2-a]-indole

A) 1-(4-Methylphenyl)pyrazolidin-3-one 10 g of p-tolylhydrazine hydrochloride are dissolved in 100 ml of anhydrous $CH_2Cl_2$. The solution is cooled to 0° C. and 19 ml of DBU and then 6.5 mg of 3-bromopropionyl chloride are added. The mixture is stirred at ambient temperature for one hour. The reaction medium is poured onto water, extraction is carried out with $CH_2Cl_2$ and then purification is carried out by chromatography on a silica column eluted with an AcOEt/petroleum ether (v/v; 50/50) mixture. 1.3 g of crystals are obtained.

NMR $CDCl_3$ (300 MHz):2.35 ppm:s:3H; 2.54 ppm:t (J=7.9):2H; 3.89 ppm:q (J=7.9):2H; 6.93-7.16 ppm:unresolved peak:4H; 8.22 ppm:s:1H.

B) 1-Acetyl-2-(4-methylphenyl)pyrazolidine 1.3 g of the compound from the preceding stage, dissolved in 20 ml of anhydrous THF, are added to 9.6 ml of a 1M solution of LAH in THF. The mixture is heated at reflux for 18 hours. It is cooled to ambient temperature, 2 ml of water and 7 ml of 1N sodium hydroxide solution are then added, and then the salts are filtered off through Celite®. The filtrate is evaporated and the residue is taken up in 20 ml of AcOEt. 2.6 g of $K_2CO_3$ and 5 ml of $H_2O$ are added, followed by 0.6 ml of acetic anhydride. The mixture is stirred at ambient temperature for one hour. The two phases are separated and the organic phase is dried over $MgSO_4$ and then evaporated to dryness. 1.4 g of oil are obtained.

NMR $CDCl_3$ (300 MHz):1.93-2.05 ppm:unresolved peak: 2H; 2.07 ppm:s 3H; 2.30 ppm:s:3H; 3.50 ppm:unresolved peak 4H; 6.83-7.11 ppm unresolved peak:4H.

C) 8-Methyl-1,2,3,4-tetrahydropyrimido[1,2-a]indole 1.4 g of the compound from the preceding stage are dissolved in 10 ml of $POCl_3$. The mixture is heated at 80° C. for one hour 30 minutes. The reaction medium is cooled, ether is added and then the precipitate formed is filtered off and washed with ether. 1.4 g of the expected compound are obtained in the form of a powder.

NMR $d_6$-DMSO (300 MHz):2.06-2.14 ppm:unresolved peak:2H; 2.33 ppm:s:3H; 3.50 ppm:unresolved peak:2H; 3.84-3.88 ppm:unresolved peak:2H; 4.15 ppm:s:2H; 7.15-7.29 ppm:unresolved peak:3H; 10.84 ppm:s:1H.

Preparation of the Intermediates of Formulae (III) and (IV)

Preparation 2.1

Methyl 2-(3,5-difluorophenyl)-3-dimethyl-amino-2-propenoate (IV)

A) Methyl (3,5-difluorophenyl)acetate

A solution comprising 25 ml of acetyl chloride in 250 ml of methanol is prepared at 0° C., then, at ambient temperature, 25.5 g of 3,5-difluorophenylacetic acid are dissolved in this solution and the solution is left stirring at AT. The reaction is monitored by thin layer chromatography. After the starting material has disappeared, the medium is evaporated under reduced pressure and then the residue is dissolved in 250 ml of MTBE. The organic phase is washed three times with 100 ml of water, dried over $MgSO_4$ and then evaporated to dryness under reduced pressure. 26.9 g of the expected compound are obtained.

B) Methyl 2-(3,5-difluorophenyl)-3-dimethylamino-2-propenoate 26.9 g of the compound from the preceding stage are dissolved in 61 ml of dimethoxy-N,N-dimethylmethanamine. The mixture is heated at 135-140° C. and the methanol formed is distilled off (12 g). The solvent is evaporated under reduced pressure and the residue is taken up in 250 ml of MTBE. The organic phase is washed three times with 50 ml of water, then dried over $MgSO_4$ and evaporated to dryness. The residue recrystallizes from methylcyclohexane. The product formed is filtered off and is then washed twice with 25 ml of methylcyclohexane to give 28 g of the expected compound, M.p.=97° C.

Preparation 2.2

Ethyl 2-(3,5-difluorophenyl)-3-hydroxy-2-propenoate (III)

A) Ethyl 3,5-difluorophenylacetate 5 g of 3,5-difluorophenylacetic acid are dissolved in 50 ml of ethanol and 3 ml of concentrated $H_2SO_4$, and the mixture is heated at reflux for two hours. The mixture is evaporated to dryness, neutralization is then carried out with a saturated $K_2CO_3$ solution, extraction is then carried out with AcOEt and the organic phase is evaporated to produce 5.0 g of the expected compound in the form of a colourless liquid.

NMR $CDCl_3$ (200 MHz):1.27 ppm:t:3H; 3.59 ppm:s:2H; 4.18 ppm:q:2H; 6.68-6.85 ppm:unresolved peak:3H.

B) Ethyl 2-(3,5-difluorophenyl)-3-hydroxy-2-propenoate 5.0 g of ethyl 3,5-difluorophenylacetate are dissolved in 50 ml of ethyl formate. 2.0 g of 60% NaH are added portionwise. The mixture is poured onto a 1N HCl solution and then extraction is carried out with AcOEt. The residue is triturated in petroleum ether, the remaining white precipitate is filtered off and then the filtrate is evaporated to produce 3.3 g of the expected compound in the form of a liquid.

NMR $CDCl_3$ (200 MHz):1.33 ppm:t:3H; 4.34 ppm:q:2H; 6.69-7.38 ppm:unresolved peak:4H; 12.16 ppm:unresolved peak:1H.

Preparation 2.3

Ethyl 2-(3,5-dimethylphenyl)-3-hydroxy-2-propenoate (III)

10 ml of ethyl 2-(3,5-dimethylphenyl)acetate are dissolved in 80 ml of ethyl formate. 5 g of 50% NaH are added portionwise and then the mixture is stirred at AT for 12 hours. The mixture is poured onto a 1N HCl solution and then extraction is carried out with AcOEt. The organic phase is evaporated to produce the expected compound, used as is in the following stage.

Preparation 2.4

Ethyl 2-(4-methoxyphenyl)-3-hydroxy-2-propenoate (III)

8.9 ml of ethyl p-methoxyphenylacetate are dissolved in 80 ml of ethyl formate. 4.6 g of 50% NaH are added portionwise and then the mixture is stirred at ambient temperature for 12 hours. It is poured onto a 1N HCl solution and then extraction is carried out with AcOEt. Purification is carried out by chromatography on a silica column eluted with an AcOEt/heptane (05/95; v/v) mixture to produce 4.0 g of the expected compound in the liquid form.

NMR $CDCl_3$ (200 MHz):1.30 ppm:t:3H; 3.83 ppm:s:3H; 4.29 ppm:q:2H; 6.89-7.21 ppm:unresolved peak:5H.

Preparation 2.5

Methyl 2-[4-(benzyloxy)phenyl]-3-dimethyl-amino-2-propenoate (IV)

200 µl of tetramethylethylenediamine are added to 5 g of methyl 2-[4-(benzyloxy)phenyl]acetate in 5.2 ml of dimethoxy-N,N-dimethylmethanamine, and the mixture is stirred at 130° C. for three hours. After cooling to AT, ethyl acetate and 60 ml of ammonium chloride are added, the mixture is stirred for five minutes, the organic phase is separated and the aqueous phase is extracted twice with ethyl acetate. After evaporating the solvent under reduced pressure and then treatment with active charcoal, 4.16 g of the expected compound are recovered after washing the solid with pentane.

NMR $CDCl_3$ (200 MHz):2.66 ppm:s:3H; 3.62 ppm:s:3H; 5.45 ppm:s:2H; 6.91 ppm:d:2H; 7.14 ppm:d:2H; 7.55 ppm: unresolved peak:5H; 7.57 ppm:s:1H.

Preparation 2.6

Ethyl 2-(3-bromophenyl)-3-hydroxy-2-propenoate (III)

A) Ethyl 3-bromophenylacetate 5 g of 3-bromophenylacetic acid are dissolved in 80 ml of ethanol, 3 ml of concentrated $H_2SO_4$ are added and then the mixture is heated at reflux for two hours. The ethanol is evaporated, neutralization is carried out with a saturated $K_2CO_3$ solution and then extraction is carried out with AcOEt. The organic phase is dried over $MgSO_4$. 5.2 g of the expected compound are obtained in the liquid form.

NMR $CDCl_3$ (300 MHz):1.18 ppm:t:3H; 3.50 ppm:s:2H; 4.08 ppm:q:2H; 7.09-7.37 ppm:unresolved peak:4H.

B) Ethyl 2-(3-bromophenyl)-3-hydroxy-2-propenoate (III)

5.2 g of the compound from the preceding stage are dissolved in 70 ml of ethyl formate, and 1.7 g of 60% NaH are added portionwise. The mixture is left stirring at AT for five hours. It is poured onto 100 ml of 1N HCl and then extraction is carried out with AcOEt. The organic phase is dried over $MgSO_4$ and then evaporated to dryness. 5.8 g of the expected compound are obtained in the form of an oil.

NMR $CDCl_3$ (300 MHz):1.9 ppm:t:3H; 4.20 ppm:q:2H; 7.11-7.42 ppm:unresolved peak:5H; 12.06 ppm:d:1H.

The intermediaries of formula (III) collated in the table below are obtained by operating according to the Preparations described above:

TABLE 2

(III)

| Preparation | $R_3$ | Characterization NMR |
|---|---|---|
| 2.7 | 2,4-diCl-phenyl | $CDCl_3$(300 MHz): 1.25 ppm: t: 3H; 4.25 ppm: q: 2H; 7.13-7.44 ppm: unresolved peak: 4H; 12.03 ppm: unresolved peak: 1H. |
| 2.8 | 3,4-diCl-phenyl | $CDCl_3$(300 MHz): 1.29 ppm: t: 3H; 4.31 ppm: q: 2H; 7.08-7.42 ppm: unresolved peak: 4H; 12.16 ppm: unresolved peak: 1H. |
| 2.9 | 3-$CF_3$-phenyl | $CDCl_3$(200 MHz): 1.30 ppm: t: 3H; 4.31 ppm: q: 2H; 7.31-7.55 ppm: unresolved peak: 4H; 12.19 ppm: unresolved peak: 1H. |
| 2.10 | 3,5-$CF_3$-phenyl | $CDCl_3$(200 MHz): 1.30 ppm: t: 3H; 4.36 ppm: q: 2H; 7.30-7.83 ppm: unresolved peak: 4H; 12.32 ppm: unresolved peak: 1H. |

TABLE 2-continued

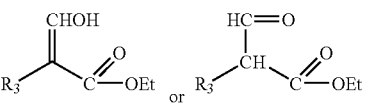

(III)

| Preparation | R₃ | Characterization NMR |
|---|---|---|
| 2.11 | 1,3-benzodioxol-5-yl | CDCl₃(200 MHz): 1.20 ppm: t: 3H; 4.33 ppm: q: 2H; 6 ppm: s: 2H; 6.7-6.9 ppm: unresolved peak: 3H; 7.29 ppm: d: 1H; 12.06 ppm: d: 1H. |
| 2.12 | 2,5-diOMe-phenyl | unpurified |
| 2.13 | 3,4-diOMe-phenyl | CDCl₃(200 MHz); 1.34 ppm: t: 3H; 3.91 and 3.92 ppm: 2s: 6H; 4.33 ppm: q: 2H; 6.7-7.0 ppm: unresolved peak: 3H; 7.32 ppm: d: 1H; 12.07 ppm: d: 1H. |
| 2.14 | 3,5-diF-phenyl | CDCl₃(200 MHz): 1.33 ppm: t: 3H; 4.34 ppm: q: 2H; 6.69-7.38 ppm: unresolved peak: 4H; 12.16 ppm: unresolved peak: 1H. |
| 2.15 | 2,4-diF-phenyl | CDCl₃(200 MHz): 1.35 ppm: t: 3H; 4.24-4.35 ppm: q: 2H; 6.82-7.30 ppm: unresolved peak: 4H; 12.16 ppm: unresolved peak: 1H. |
| 2.16 | 2,3-diF-phenyl | CDCl₃(200 MHz): 1.30 ppm: t: 3H; 4.30 ppm: q: 2H; 6.96-7.34 ppm: unresolved peak: 4H; 12.24 ppm: d: 1H. |
| 2.17 | 3,5-diCl-phenyl | CDCl₃(200 MHz): 1.26 ppm: t: 3H; 4.29 ppm: q: 2H; 7.16-7.49 ppm: unresolved peak: 4H. |
| 2.18 | 3-F, 5-CF₃-phenyl | CDCl₃(200 MHz): 1.32 ppm: t: 3H; 4.31 ppm: q: 2H; 7.21-7.40 ppm: unresolved peak: 4H; 12.26 ppm: unresolved peak: 1H. |
| 2.19 | 2,4-diF-phenyl | CDCl₃(200 MHz): 1.35 ppm: t: 3H; 4.24-4.35 ppm: q(J=7.1): 2H; 6.82-7.30 ppm: unresolved peak: 4H; 12.16 ppm: unresolved peak: 1H. |
| 2.20 | 4-SO₂Me-phenyl | Oil |
| 2.21 | (4-OMe, 3,5-di-tBu)phenyl | 1.38 ppm: t(J=7.2): 3H; 1.56 ppm: s: 18H; 3.83 ppm: s: 3H; 4.41 ppm: q(J=7.2): 2H; 7.27-7.44 ppm: unresolved peak: 3H; 12.21: d (J=12.7): 1H. |
| 2.22 | 3,4,5-triOMe-phenyl | CDCl₃(200 MHz): 1.36 ppm: t (J=7.1): 3H; 3.88, 3.89 and 3.90 ppm: 3s: 9H; 4.35 ppm: q (J=7.1): 2H; 6.53 ppm: s: 2H; 7.36 ppm: d(J=12.7): 1H; 12.12 ppm: d (J=7.1): 1H. |
| 2.23 | 3,5-diOMe-phenyl | CDCl₃(300 MHz): 1.32 ppm: t: 3H; 3.80 ppm: s: 6H; 4.27-4.34 ppm: q (J=7.2): 2H; 6.49 ppm: unresolved peak: 3H; 7.34 ppm: d: 1H; 12.14 ppm: d(J=12.5): 1H |
| 2.24 | 4-N₃-phenyl | d6-DMSO(200 MHz): 1.1 ppm: t: 3H; 4 ppm: q: 2H; 7 ppm: d: 2H; 7.3 ppm: d: 2H; 7.8 ppm: s: 1H; 11 ppm: s: 1H |
| 2.25 | 2,4-diOMe-phenyl | |
| 2.26 | 3-N₃-phenyl | d₆-DMSO(200 MHz): 1.2 ppm: t: 3H; 4.1 ppm: q: 2H; 7 ppm: s: 1H; 7.05 ppm: d: 1H; 7.2 ppm: d: 1H; 7.35 ppm: unresolved peak: 2H; 7.9 ppm: s: 1H. |
| 2.27 | 2-Cl, 4-F-phenyl | CDCl₃(300 MHz): 1.16 ppm: t (J=7.2): 3H; 4.13 ppm: q (J=7.2): 2H; 6.89-7.90 ppm: unresolved peak: 4H; 11.90 ppm: d (J=12.7): 1H |

Preparation 2.28

Ethyl 2-(6-chloro-1,3-benzodioxol-5-yl)-3-hydroxy-acrylate

A) 5-Bromomethyl-6-chloro-1,3-benzodioxole 2.5 g of 6-chloropiperonyl alcohol are dissolved in 80 ml of ethyl ether. The solution is cooled to 0° C. and then 1.9 ml of PBr₃ are added. The mixture is stirred at ambient temperature for 18 hours. It is poured onto ice and then extraction is carried out with AcOEt. The organic phase is washed with a saturated NaCl solution. 3.3 g of powder are obtained.

NMR CDCl₃ (300 MHz):4.47 ppm:s:2H; 5.92 ppm:s:2H; 6.77 ppm:s:1H; 6.88 ppm:s:1H.

B) (6-Chloro-1,3-benzodioxol-5-yl)acetonitrile 3.3 g of the compound from the preceding stage are dissolved in 70 ml of ethanol and 15 ml of water. 1.8 g of KCN are added and then the mixture is heated at reflux for 5 hours. The ethanol is evaporated, the residue is taken up in water and then extraction is carried out with AcOEt. The organic phase is dried over MgSO₄ and then evaporated to dryness. 2.4 g of oil are obtained.

NMR CDCl₃ (300 MHz):3.75 ppm:s:2H; 6.02 ppm:s:2H; 6.88 ppm:s:1H; 6.95 ppm:s:1H.

C) Ethyl (6-chloro-1,3-benzodioxol-5-yl)acetate 2.4 g of compound from the preceding stage are dissolved in 80 ml of ethanol and 4 ml of concentrated H₂SO₄. The mixture is heated at reflux for 48 hours. The ethanol is evaporated, the residue is taken up in water and then extraction is carried out with AcOEt. The organic phase is washed with a saturated NaCl solution, dried over MgSO₄ and then evaporated to dryness. 2.9 g of oil are obtained, which oil comprises approximately 20% of starting material.

NMR CDCl₃ (300 MHz):1.26 ppm:t (J=6.9):3H; 3.68 ppm:s:2H; 4.15-4.23 ppm:q (J=6.9):2H; 5.98 ppm:s:2H; 6.77 ppm:s:1H; 6.87 ppm:s:1H.

D) Ethyl 2-(6-chloro-1,3-benzodioxol-5-yl)-3-hydroxyacrylate 2.9 g of compound from the preceding stage are dissolved in 60 ml of ethyl formate. 1.0 g of 60% NaH is added and then the mixture is stirred at ambient temperature for 5 hours. It is poured onto 100 ml of a 1N HCl solution and then extraction is carried out with AcOEt. The organic phase is dried over MgSO₄ and evaporated to dryness. 3.2 g of oil are obtained, which oil is used as is for the continuation.

Preparation 2.29

Ethyl 2-(3-hydroxyphenyl)-3-dimethylamino-acrylate

A) Methyl (3-hydroxyphenyl)acetate 10 g of 3-hydroxyphenylacetic acid are dissolved in 60 ml of methanol and 2.5 ml of sulphuric acid. The solution is heated at reflux for two hours. It is brought back to ambient temperature and the methanol is evaporated. The residue is taken up in a saturated K₂CO₃ solution. Extraction is carried out with AcOEt. The organic phase is dried over MgSO₄, filtered and evaporated to dryness. 11.1 g of oil are obtained.

NMR d₆-DMSO (300 MHz):3.57 ppm:s:3H; 3.61 ppm:s: 2H; 6.66 ppm:unresolved peak:3H; 7.09 ppm:unresolved peak:1H; 9.42 ppm:s:1H.

B) Ethyl (3-benzyloxyphenyl)acetate 3 g of the compound from the preceding stage are dissolved in 13 ml of ethanol. 3.75 g of $K_2CO_3$, 3.12 ml of benzyl chloride and a spatula tip of $nBu_4NI$ are added. The mixture is heated at reflux for 6 hours. It is brought back to ambient temperature, filtration through $K_2CO_3$ is carried out and evaporation to dryness is carried out. The residue is taken up in AcOEt and the organic phase is washed with water. 5 g of oil are obtained.

NMR $d_6$-DMSO (300 MHz):1.19 ppm:t:3H; 3.64 ppm:s: 2H; 5.08 ppm:s:2H; 6.85-6.98 ppm:unresolved peak:2H; 7.22-7.51 ppm:unresolved peak:7H.

C) Ethyl 2-(3-hydroxyphenyl)-3-dimethylaminoacrylate 5 g of the compound from the preceding stage are dissolved in 8 ml of dimethylformamide dimethyl acetal (DMFDMA). The solution is heated at 135° C. for 24 hours while adding 1 ml of DMFDMA every three hours approximately. The mixture is evaporated to dryness. 6 g of oil are obtained.

The intermediates of formula (IV) collated in the table below are obtained by operating according to Preparation 2.1:

TABLE 3

(IV)

[Structure: $R_3$-HC=C(N(CH_3)_2)(C(=O)-O-CH_3)]

| Preparation | $R_3$ | Characterization NMR |
|---|---|---|
| 3.1 | 4-NMe$_2$-phenyl | |
| 3.2 | 2,6-diCl-phenyl | $d_6$-DMSO(200 MHz): 2.8 ppm: s: 6H; 3.5 ppm: s: 3H; 7.3-7.55 ppm: unresolved peak: 3H; 7.6 ppm: s: 1H. |
| 3.3 | 3-Br, 4-OMe-phenyl | 125° C. |
| 3.4 | 2,4-diCl-phenyl | $d_6$-DMSO(200 MHz): 2.6 ppm: s: 6H; 3.4 ppm: s: 3H; 7.1-7.3 ppm: unresolved peak: 2H; 7.4-7.5 ppm: unresolved peak: 2H. |
| 3.5 | 2-Br, 4,5-diOMe-phenyl | 115° C. |
| 3.6 | 2-Cl, 4,5-diOMe-phenyl | $d_6$-DMSO(200 MHz): 2.6 ppm: s: 6H; 3.4 ppm: s: 3H; 3.6 ppm: s: 3H; 3.65 ppm: s: 3H; 6.65 ppm: s: 1H; 6.85 ppm: s: 1H; 7.4 ppm: s: 1H. |
| 3.7 | 3-CN, 4-OMe-phenyl | 125° C. |
| 3.8 | 2,4-diMe-phenyl | — |
| 3.9 | 3,4-diMe-phenyl | — |
| 3.10 | 4-OBn-phenyl | $d_6$-DMSO/TFA(200 MHz): 2.6 ppm: s: 6H; 3.4 ppm: s: 3H; 5 ppm: s: 2H; 6.8-7 ppm: unresolved peak: 4H; 7.1-7.25 ppm: unresolved peak: 6H. |
| 3.11 | 4-(OCH$_2$COOMe)-phenyl | $d_6$-DMSO(300 MHz): 2.64 ppm: s: 6H; 3.50 ppm: s: 3H; 3.70 ppm: s: 3H; 4.75 ppm: s: 2H; 6.64-7.48 ppm: unresolved peak: 4H; 7.95 ppm: s: 1H. |
| 3.12 | 3,5-diOMe-phenyl | CDCl$_3$(300 MHz): 2.30 ppm: s: 6H; 2.68 ppm: s: 6H; 3.64 ppm: s: 3H; 6.81-6.86 ppm: unresolved peak: 3H; 7.54 ppm: s: 1H |

Preparation 3.13

Ethyl 2-(4-bromo-2-chlorophenyl)-3-dimethyl-aminoacrylate

A) 4-Bromo-1-bromomethyl-2-chlorobenzene 5.0 g of 2-chloro-4-bromotoluene are dissolved in 120 ml of $CCl_4$. 4.3 g of NBS and 1.6 g of AIBN are added. The mixture is heated at reflux for 15 hours, water is added, the two phases are separated and then extraction is carried out with $CH_2Cl_2$. Purification is carried out by chromatography on a silica column eluted with petroleum ether. 3.8 g of liquid are obtained.

CDCl$_3$ (300 MHz):4.48 ppm:s:2H; 7.23-7.36 ppm:unresolved peak:2H; 7.51 ppm:s:1H.

B) (4-Bromo-2-chlorophenyl)acetonitrile 3.8 g of the compound from the preceding stage are dissolved in 70 ml of ethanol and 15 ml of $H_2O$. 1.7 g of KCN are added and then the mixture is heated at reflux for 5 hours. The ethanol is evaporated, the residue is taken up in water and then extraction is carried out with AcOEt. 2.5 g of oil are obtained.

CDCl$_3$ (300 MHz):3.79 ppm:s:2H; 7.35-7.49 ppm:unresolved peak:2H; 7.59 ppm:s:1H.

C) Ethyl (4-bromo-2-chlorophenyl)acetate 2.5 g of the compound from the preceding stage are dissolved in 80 ml of ethanol and 4 ml of concentrated $H_2SO_4$. The solution is heated at reflux for four days. The ethanol is evaporated, the residue is taken up in a saturated $K_2CO_3$ solution, and the organic phase is dried over MgSO$_4$ and then evaporated to dryness. 2.5 g of liquid are obtained.

CDCl$_3$ (300 MHz):1.28 ppm:t (J=7.1):3H; 3.73 ppm:s:2H; 4.18 ppm:q (J=7.1):2H; 7.18 ppm: unresolved peak:1H; 7.38 ppm:unresolved peak:1H; 7.56 ppm:s:1H.

D) Ethyl 2-(4-bromo-2-chlorophenyl)-3-dimethyl-aminoacrylate 2.8 g of the compound from the preceding stage are dissolved in 3.1 g of Bredereck's reagent. The solution is heated at 100° C. for 15 hours and the excess reagent is evaporated. 2.9 g of oil are obtained.

CDCl$_3$ (300 MHz):1.18 ppm:t (J=7.1):3H; 2.72 ppm:s:6H; 4.09 ppm:q (J=7.1):2H; 7.15 ppm:unresolved peak:1H; 7.35 ppm:unresolved peak:1H; 7.54 ppm:unresolved peak:1H; 7.60 ppm:s:1H.

EXAMPLE 1

Compound 6

3-(3,5-Difluorophenyl)-1,6,9-trimethyl-1,9-dihydro-2H-pyrido[2,3-b]indol-2-one 25 g of the compound from Preparation 2.1 and 22.5 g of the compound from Preparation 1.1 are mixed in 75 ml of acetic acid and the mixture is heated at 40° C. for 24 hours and then at 60-65° C. for 4 hours. The reaction medium is cooled to AT and is then poured onto 275 ml of water. The precipitate formed is recovered, washed with 50 ml of water and then recrystallized from 250 ml of MIBK. The residual water is removed by azeotropic distillation at atmospheric pressure. The product obtained is washed twice with 25 ml of MiBK and then dried at 40-45° C. under reduced pressure for 24 hours to give 20.33 g of the expected compound after crystallization from MiBK (20.33 g), M.p.=240° C. NMR $d_6$-DMSO (200 MHz):2.51 ppm:s:3H; 4.05 ppm:s:6H; 6.69-8.08 ppm:unresolved peak:7H.

EXAMPLE 2

Compound 22

3-(3,5-Difluorophenyl)-1,6-dimethyl-1,9-dihydro-2H-pyrido[2,3-b]indol-2-one 1.5 g of hydrochloride from Preparation 1.2 are dissolved in 50 ml of pyridine. 1.9 g of the compound from Preparation 2.2 are added and the mixture is heated at 70° C. for 20 hours. The mixture is evaporated to dryness and the residue is then taken up in water and extracted with $CH_2Cl_2$. Purification is carried out by chromatography on a silica column eluted with an AcOEt/heptane (50/50; v/v) mixture to produce 300 mg of the expected compound in the form of a powder, M.p.=189° C. (decomposition).

NMR $d_6$-DMSO (300 MHz):2.51 ppm:s:3H; 3.70 ppm:s:3H; 7.04-8.68 ppm:unresolved peak:7H; 11.98 ppm:s:1H.

EXAMPLE 3

Compound 16

1,6-Dimethyl-3-(3,5-dimethylphenyl)-1,9-dihydro-2H-pyrido[2,3-b]indol-2-one 0.8 g of the compound from Preparation 1.2 is dissolved in 50 ml of pyridine. 0.8 g of compound from Preparation 2.3 is added and the mixture is heated at 80° C. for 20 hours. The mixture is evaporated to dryness and then the residue is taken up in water and extracted with $CH_2Cl_2$. Purification is carried out by chromatography on a silica column eluted with an AcOEt/heptane (50/50; v/v) mixture to produce 500 mg of the expected compound, after recrystallization from isopropanol.

NMR $d_6$-DMSO (200 MHz):2.23 ppm:s:6H; 2.49 ppm:s:3H; 3.73 ppm:s:3H; 6.84-8.08 ppm:unresolved peak:7H; 9.98 ppm:s:1H.

EXAMPLE 4

Compound 20

6-Methoxy-1,9-dimethyl-3-(3,5-difluorophenyl)-1,9-dihydro-2H-pyrido[2,3-b]indol-2-one 2.5 g of the compound from Preparation 1.3 are dissolved in 70 ml of pyridine. 3.3 g of the compound from Preparation 2.2 are added and the mixture is heated at 100° C. for 20 hours. The mixture is evaporated to dryness and then the residue is taken up in water and AcOEt. The remaining precipitate is filtered off. Recrystallization is carried out from isopropanol to produce 1.35 g of the expected compound, M.p.=189° C.

NMR $CDCl_3$ (200 MHz):3.91 ppm:s:3H; 4.04 ppm:s:6H; 6.68-8.05 ppm:unresolved peak:7H.

EXAMPLE 5

Compound 1

3-(3,5-Dimethylphenyl)-1,6,9-trimethyl-1,9-dihydro-2H-pyrido[2,3-b]indol-2-one

This compound is prepared from the compounds of Preparations 1.1 and 2.3, M.p.=210° C.

NMR $CDCl_3$ (200 MHz):2.42 ppm:s:6H; 2.54 ppm:s:3H; 4.07 ppm:s:6H; 7.00-8.08 ppm:unresolved peak:7H.

EXAMPLE 6

Compound 2

3-(2,4-Dichlorophenyl)-1,6,9-trimethyl-1,9-dihydro-2H-pyrido[2,3-b]indol-2-one

This compound is prepared from the compounds of Preparations 1.1 and 2.7, M.p.=170° C.

NMR $CDCl_3$ (300 MHz):2.51 ppm:s:3H; 4.09 ppm:s:3H; 4.11 ppm:s:3H; 7.15-8.00 ppm:unresolved peak:7H.

EXAMPLE 7

Compound 21

3-(2,4-Dichlorophenyl)-6-methoxy-1,9-dimethyl-1,9-dihydro-2H-pyrido[2,3-b]indol-2-one This compound is prepared from the compounds of Preparations 1.3 and 2.7, M.p.=130° C.

NMR $CDCl_3$ (300 MHz):3.90 ppm:s:3H; 4.07 ppm:s:3H; 4.09 ppm:s:3H; 6.93-7.98 ppm:unresolved peak:7H.

EXAMPLE 8

Compound 32

3-(2,4-Dichlorophenyl)-1,5,7,9-tetramethyl-1,9-dihydro-2H-pyrido[2,3-b]indol-2-one This compound is prepared from the compounds of Preparations 1.11 and 2.7, M.p.=204° C.

NMR $CDCl_3$ (300 MHz):2.51 ppm:s:3H; 2.68 ppm:s:3H; 4.10 ppm:s:6H; 6.91 ppm:s:1H; 7.05 ppm:s:1H; 7.31 ppm:dd:1H; 7.44 ppm:d:1H; 7.52 ppm:d:1H; 8.11 ppm:s:1H.

EXAMPLE 9

Compound 66

3-(4-Hydroxyphenyl)-1,6,9-trimethyl-1,9-dihydro-2H-pyrido[2,3-b]indolone

A) 3-(4-Methoxyphenyl)-1,6,9-trimethyl-1,9-dihydro-2H-pyrido[2,3-b]indolone 2.0 g of hydrochloride obtained in Preparation 1.1 are dissolved in 50 ml of pyridine. 2.1 g of formyl ester obtained in Preparation 2.4 are added and the mixture is heated at 80° C. for 20 hours. The mixture is evaporated to dryness, then extraction is carried out with $CH_2Cl_2$ and washing is carried out with water. Purification is carried out by chromatography on a silica column eluted with an AcOEt/heptane/$CH_2Cl_2$ (50/50/50; v/v/v) mixture to produce 0.5 g of the expected compound in the form of a powder.

NMR $d_6$-DMSO (200 MHz):2.50 ppm:s:3H; 3.86 ppm:s:3H; 4.05 ppm:s:6H; 6.96-8.04 ppm:unresolved peak:8H.

B) 3-(4-Hydroxyphenyl)-1,6,9-trimethyl-1,9-dihydro-2H-pyrido[2,3-b]indolone 18 ml of $BBr_3$, in solution in DCM, are added, with stirring and at −78° C., to 5.36 g of the compound from the preceding stage dissolved in 60 ml of DCM. The mixture is allowed to return to ambient temperature. This mixture is subsequently stirred at this temperature for 24 hours. The reaction medium is diluted with a mixture of DCM and MeOH. The solution is evaporated under reduced pressure. The crude product is taken up in DCM and adsorbed on 16 g of silica and chromatographed on a silica column with a (97/3; v/v) then (95/5; v/v) up to (50/50; v/v) DCM/MeOH mixture. A solid is thus recovered and suspended in a DCM/MeOH mixture. The suspension obtained is cooled and filtered. The precipitate is then collected. 4 g of the expected compound are thus recovered, comprising 4% of starting compound, M.p.>280° C.

NMR $d_6$-DMSO (200 MHz):2.3 ppm:s:3H; 3.9 ppm:s:3H; 4 ppm:s:3H; 6.6 ppm:d:2H; 7 ppm:d:1H; 7.3 ppm:d:1H; 7.5 ppm:d:2H; 7.6 ppm:s:1H; 8.1 ppm:s:1H.

EXAMPLE 10

Compound 68

1,6-Dimethyl-3-(4-hydroxyphenyl)-1,9-dihydro-2H-pyrido[2,3-b]indolone

A) 1,6-Dimethyl-3-(4-benzyloxyphenyl)-1,9-dihydro-2H-pyrido[2,3-b]indolone 1 g of N,5-dimethyl-1H-indole-2-amine (Preparation 1.2) is mixed with 1.4 g of the compound from Preparation 2.5 and 10 ml of acetic acid, and then the mixture is heated at 100° C. for 18 hours. The mixture is evaporated to dryness under vacuum and then the residue is taken up in 20 ml of $CH_2Cl_2$ and 5 ml of $H_2O$. The pH is brought to 7 with 1N NaOH with stirring, the two layers are then separated by settling and the organic phase is washed with NaCl and then dried and evaporated to dryness. The residue is taken up in 10 ml of $Et_2O$, filtration is carried out and then the organic phase is washed and dried.

B) 1,6-Dimethyl-3-(4-hydroxyphenyl)-1,9-dihydro-2H-pyrido[2,3-b]indolone 0.800 g of the compound from the preceding stage and 50 ml of TFA are mixed. The mixture is heated at 75° C. for 1 hour 30 minutes. The mixture is evaporated to dryness under vacuum and then the residue is taken up in 15 ml of $Et_2O$ and drying is carried out, M.p.=186° C.

NMR $d_6$-DMSO (300 MHz):2.6 ppm:s:3H; 3.8 ppm:s:3H; 6.8 ppm:d:2H; 7.1 ppm:d:1H; 7.4 ppm:d:1H; 7.6 ppm:d:2H; 7.8 ppm:s:1H; 8.2 ppm:s:1H; 11.9 ppm:s:1H.

EXAMPLE 11

Compound 52

4-(1,6,9-Trimethyl-2-oxo-2,9-dihydro-1H-pyrido[2,3-b]indol-3-yl)benzonitrile

A) 3-(3-Bromophenyl)-1,6,9-trimethyl-1,9-dihydro-2H-pyrido[2,3-b]indol-2-one 2.5 g of the compound from Preparation 1.1 are dissolved in 40 ml of acetic acid and 60 ml of pyridine; 3.5 g of the compound from Preparation 2.6 are added and then the mixture is heated at 100° C. for 15 hours. The reaction medium is poured into 200 ml of water and the precipitate formed is filtered off. The latter is taken up in $CH_2Cl_2$ and then washed with a saturated NaCl solution, dried over $MgSO_4$ and evaporated to dryness. The precipitate is taken up in an AcOEt/cyclohexane (20/8; v/v) mixture and is then filtered. 20 g of the expected compound are obtained, M.p.=215-216° C.

B) 4-(1,6,9-Trimethyl-2-oxo-2,9-dihydro-1H-pyrido[2,3-b]indol-3-yl)benzonitrile 3 g of the compound obtained in the preceding stage are dissolved in 50 ml of 1-methyl-2-pyrrolidinone, 1.4 g of CuCN are added and then the mixture is heated at 200° C. for 4 hours. The reaction medium is poured onto 100 ml of $CH_2Cl_2$ and then the precipitate formed is filtered off. The filtrate is washed with a 1N HCl solution and is then dried over $MgSO_4$. The product obtained is purified by chromatography on silica, elution being carried out with AcOEt/$CH_2Cl_2$ (50/50; v/v) and then AcOEt/MeOH/$NH_3$ (90/10/1; v/v/v). 2.2 g of the expected compound are collected in the form of a powder.

NMR $CDCl_3$ (300 MHz):2.52 ppm:s:3H; 4.09 ppm:s:3H; 4.12 ppm:s:3H; 7.16 ppm:unresolved peak:8H.

EXAMPLE 12

Compound 53

3-(4-(Aminomethyl)phenyl)-1,6,9-trimethyl-1,9-dihydro-2H-pyrido[2,3-b]indol-2-one 50 mg of sodium hydroxide are dissolved in 11 ml of ethanol, 0.2 g of the compound obtained in the preceding example are added, followed by approximately 100 mg of Raney Ni, and the mixture is hydrogenated for 24 hours under 50 psi. The catalyst is filtered off through Celite®, rinsing is then carried out with methanol and evaporation is carried out to dryness. The residue is taken up in a 1N HCl solution and then the impurities are extracted with AcOEt. The solution is basified to pH=9 with a $K_2CO_3$ solution and then extraction is carried out with AcOEt to produce 90 mg of the expected compound in the form of a powder.

NMR $CDCl_3$ (300 MHz):2.51 ppm:s:3H; 3.91 ppm:s:2H; 4.08 ppm:s:6H; 7.13-8.09 ppm:unresolved peak:8H.

EXAMPLE 13

Compound 84

Methyl (3-(2,4-dichlorophenyl)-1,6-dimethyl-2-oxo-1,2-dihydro-9H-pyrido[2,3-b]indol-9-yl)acetate 1 g of 3-(2,4-dichlorophenyl)-1,6-dimethyl-1,9-dihydro[2,3-b]indol-2-one (compound 46) is dissolved in 10 ml of DMF, 0.143 g of 95% NaH is added and, after stirring for 30 minutes, 0.4 ml of methyl bromoacetate is added. After stirring for one hour at AT, the reaction mixture is evaporated and then the residue is taken up in $CH_2Cl_2$ and washed with a $NaHCO_3$ solution and then a NaCl solution. The organic phase is dried and then evaporated to produce 0.98 g of the expected product.

EXAMPLE 14

Compound 85

2-(3-(2,4-Dichlorophenyl)-1,6-dimethyl-2-oxo-1,2-dihydro-9H-pyrido[2,3-b]indol-9-yl)-N-methyl-acetamide 0.3 g of the ester obtained in the preceding example and 30 ml of 33% methylamine in EtOH are mixed. After stirring at AT for 5 hours, the reaction medium is evaporated and the residue is taken up in $Et_2O$ and then filtration and drying are carried out to produce 0.260 g of the expected compound.

EXAMPLE 15

Compound 81

3-(3-Hydroxymethylphenyl)-1,6-dimethyl-1,9-dihydro-2H-pyrido[2,3-b]indol-2-one

A) 3-(1,6-Dimethyl-2-oxo-2,9-dihydro-1H-pyrido[2,3-b]indol-3-yl)benzaldehyde 450 mg of 3-(3-cyanophenyl)-1,6-dimethyl-1,9-dihydro-2H-pyrido[2,3-b]indol-2-one, 10 ml of AcOH, 20 ml of pyridine, 2.6 g of sodium hypophosphite and 434 mg of Raney Ni are mixed and then the mixture is heated at 60° C. for 4 hours. The reaction medium is filtered and the filtrate is evaporated; the residue is taken up in 50 ml of AcOEt/CH$_2$Cl$_2$ (1/1; v/v) and the organic phase is washed with water, dried and evaporated to produce the expected compound, M.p.=280° C.

B) 3-(3-Hydroxymethylphenyl)-1,6-dimethyl-1,9-dihydro-2H-pyrido[2,3-b]indol-2-one 280 mg of the compound obtained in Stage A are placed in 10 ml of CH$_2$Cl$_2$ and the minimum amount of AcOH to dissolve the compound, 375 mg of NaBH(OAc)$_3$ are added and then the mixture is left stirring at AT for 18 hours. The reaction medium is evaporated and the residue is taken up in AcOEt and then filtration is carried out to produce 200 mg of the expected compound.

EXAMPLE 16

Compound 80

1,6-Dimethyl-3-(3-((methylamino)methyl)-phenyl)-1,9-dihydro-2H-pyrido[2,3-b]indol-2-one 280 mg of the compound from Stage A of the preceding example are placed in 10 ml of CH$_2$Cl$_2$ and the minimum amount of AcOH to dissolve the compound and then 375 mg of NaBH(OAc)$_3$ and 0.064 ml of methylamine are added. After stirring at AT for 18 hours, extraction is carried out three times with 10 ml of water and then the aqueous phase is extracted with AcOEt. After evaporating, 15 mg of the expected compound are obtained.

EXAMPLE 17

Compound 83

3-(1,6-Dimethyl-2-oxo-2,9-dihydro-1H-pyrido[2,3-b]indol-3-yl)benzaldehyde oxime 210 mg of the compound from Example 15, Stage A, are dissolved in 5 ml of MeOH, 46 mg of hydroxylamine hydrochloride, in solution in the minimum amount of water, are added and the mixture is left stirring at AT for two hours. The mixture is evaporated to dryness and then the residue is chromatographed on silica, elution being carried out with AcOEt/CH$_2$Cl$_2$ (2/8; v/v). 74 mg of the expected compound are obtained.

EXAMPLE 18

Compound 110

1,6-Dimethyl-3-(3-methoxycarbonylphenyl)-1,9-dihydro-2H-pyrido[2,3-b]indol-2-one A) 3-(3-Bromophenyl)-1,6-dimethyl-1,9-dihydro-2H-pyrido[2,3-b]indol-2-one This compound is prepared according to the usual methods by reaction of N,1,5-trimethyl-1H-indole-2-amine with ethyl 2-(3-bromophenyl)-3-hydroxy-2-propenoate.

NMR d$_6$-DMSO (200 MHz):2.42 ppm:s:3H; 3.69 ppm:s:3H; 7.04 ppm:d:1H; 7.35 ppm:d:1H; 7.05-7.08 ppm:unresolved peak:5H; 8.30 ppm:s:1H; 11.91 ppm:s:1H.

B) 1,6-Dimethyl-3-(3-methoxycarbonylphenyl)-1,9-dihydro-2H-pyrido[2,3-b]indol-2-one 500 mg of the compound from the preceding stage and 140 mg of 1,3-bis(diphenylphosphino)propane are dissolved in 20 ml of anhydrous MeOH. 1.9 ml of 99.9% triethylamine, 15 ml of anhydrous DMSO and then 60 mg of Pd(OAc)$_2$ are added. CO is bubbled into the reaction medium for 20 minutes and the medium is heated at 75° C. overnight under a CO atmosphere. The medium is allowed to return to ambient temperature. The reaction medium is poured onto 200 ml of water and is then extracted with AcOEt. The organic phase is dried over MgSO$_4$, filtered and evaporated to dryness. The residue is purified on a silica column eluted with an AcOEt/petroleum ether (v/v; 75/25) mixture. The precipitate obtained is triturated with an AcOEt/petroleum ether mixture. 260 mg of a powder are obtained.

NMR d$_6$-DMSO (300 MHz):2.43 ppm:s:3H; 3.70 ppm:s:3H; 3.88 ppm:s:3H; 7.05 ppm:unresolved peak:1H; 7.35 ppm:d (J=8):1H; 7.54 ppm:unresolved peak:1H; 7.74 ppm:unresolved peak:1H; 7.86 ppm:unresolved peak:1H; 8.02 ppm:unresolved peak:1H; 8.43 ppm:unresolved peak:1H; 11.94 ppm:s:1H.

EXAMPLE 19

Compound 111

3-(4-Aminophenyl)-1,6-dimethyl-1,9-dihydro-2H-pyrido[2,3-b]indol-2-one

A) 3-(4-Bromophenyl)-1,6-dimethyl-1,9-dihydro-2H-pyrido[2,3-b]indol-2-one

This compound is prepared according to the usual methods by reaction of N,1,5-trimethyl-1H-indole-2-amine with ethyl 2-(4-bromophenyl)-3-hydroxy-2-propenoate.

NMR d$_6$-DMSO (300 MHz):2.35 ppm:s:3H; 3.61 ppm:s:3H; 3.97 ppm:d:1H; 7.03 ppm:d:1H; 7.45-7.80 ppm:unresolved peak:5H; 8.32 ppm:s:1H; 11.85 ppm:s:1H.

B) 3-(4-Aminophenyl)-1,6-dimethyl-1,9-dihydro-2H-pyrido[2,3-b]indol-2-one 10 ml of THF are degassed for 10 minutes and 9.2 mg of Pd$_2$(dba)$_3$, then 370 mg of the compound from the preceding stage, then 9.4 mg of ligand 2-dicyclo-hexylphosphino-2'-(N,N-dimethylamino)biphenyl and, finally, 2.2 ml of a 1M solution of LiN(TMS)$_2$ in THF are added under argon. The mixture is stirred in a sealed tube at 90° C. for 20 hours. The reaction medium is cooled, then 10 ml of a 1N HCl solution are added and then the mixture is stirred at ambient temperature for 10 minutes. The two phases are separated and the aqueous phase is washed with AcOEt and then basified with a saturated $K_2CO_3$ solution. The precipitate formed is filtered off. 90 mg are obtained.

NMR $d_6$-DMSO (300 MHz):2.40 ppm:s:3H; 3.65 ppm:s: 3H; 4.99 ppm:s:2H; 6.57 ppm:unresolved peak:2H; 6.94 ppm:d (J=8.1):1H; 7.29 ppm:d (J=8.1):1H; 7.43 ppm:unresolved peak:2H; 7.60 ppm:s:1H; 8.07 ppm:s:1H.

EXAMPLE 20

Compound 121

1,6-Dimethyl-1,9-dihydro-3-(phenylamino-phenyl)-2H-pyrido[2,3-b]indol-2-one 13 mg of $Pd_2(dba)_3$, 500 mg of the compound from Example 18, Stage A, 11 mg of ligand 2-dicyclo-hexylphosphino-2'-(N,N-dimethylamino)biphenyl, 3 ml of a 1M solution of LiN(TMS)$_2$ in THF, 127 mg of aniline and then 10 ml of anhydrous dioxane are placed under argon. The mixture is stirred in a sealed tube at 65° C. for 24 hours. The mixture is brought back to ambient temperature and then AcOEt is added. The organic phase is washed with a saturated NaCl solution. Purification is carried out on a silica column eluted with an AcOEt/petroleum ether (v/v; 50/50) then (v/v; 75/25) mixture. The precipitate obtained is triturated in ether. 55 mg of the expected compound are obtained in the form of a precipitate, M.p.=188-190° C.

NMR $d_6$-DMSO (300 MHz):2.42 ppm:s:3H; 3.68 ppm:s: 3H; 6.77-8.28 ppm:unresolved peak:14H; 12.00 ppm:s:1H.

EXAMPLE 21

Compound 147

3-(2,4-Dicyanophenyl)-1,6-dimethyl-1,9-dihydro-2H-pyrido[2,3-b]indol-2-one 0.6 g of 3-(2-chloro-4-bromophenyl)-1,6-dimethyl-1,9-dihydro-2H-pyrido[2,3-b]indol-2-one is dissolved in 15 ml of NMP. 0.27 g of CuCN is added and then the mixture is heated at reflux for 5 hours. The reaction medium is poured onto $CH_2Cl_2$ and washing is carried out with a saturated NaCl solution. Purification is carried out by chromatography on a silica column eluted with an AcOEt/petroleum ether (v/v; 75/25) mixture and then pure AcOEt. The fractions recovered are washed with a 1N HCl solution to remove an NMP residue. 50 mg of the expected compound are obtained in the form of a powder.

NMR $d_6$-DMSO (300 MHz):2.27 ppm:s:3H; 3.70 ppm:s: 3H; 7.08 ppm:d (J=8.1):1H; 7.38 ppm:d(J=8.1):1H; 7.67 ppm:s:1H; 7.85 ppm:d(J=8.2):1H; 8.15 ppm:d(J=8.2):1H; 8.45 ppm:unresolved peak:2H; 12.11 ppm:s:1H.

EXAMPLE 22

Compound 143

3-(3-Acetylphenyl)-1,6-dimethyl-1,9-dihydro-2H-pyrido[2,3-b]indol-2-one 400 mg of Compound 60 are dissolved in 20 ml of anhydrous THF. The reaction medium is cooled to 0° C. and then 9.1 ml of 1.4M $CH_3Li$ in THF are added portionwise. The mixture is allowed to return to ambient temperature and is then stirred for 2 hours. The reaction medium is poured onto 1N HCl and washing is then carried out with AcOEt. The aqueous phase is basified with 5N NaOH and then the product is extracted with AcOEt. The organic phase is dried over $MgSO_4$, filtered and evaporated to dryness. The residue is purified on a silica column eluted with an AcOEt/petroleum ether (v/v; 80/20) mixture and then with pure AcOEt. 40 mg of the expected compound are obtained, M.p.=258-260° C.

NMR $d_6$-DMSO (300 MHz):2.43 ppm:s:3H; 2.63 ppm:s: 3H; 3.70 ppm:s:3H; 7.03-8.43 ppm:unresolved peak:8H; 11.92 ppm:s:1H.

EXAMPLE 23

Compound 127

1,6-Dimethyl-3-(3-(pyridin-2-ylamino)phenyl)-1,9-dihydro-2H-pyrido[2,3-b]indol-2-one 500 mg of the compound from Example 18, Stage A, 180 mg of 2-aminopyridine, 315 mg of NaOtBu, 50 mg of $Pd_2$(dba)$_3$ and 95 mg of Xant phos are dissolved in 7 ml of dioxane (in a sealed tube). The reaction medium is degassed for 30 minutes and is then heated at 100° C. overnight. It is brought back to ambient temperature. After purifying on a silica column eluted with ethyl acetate, 380 mg of powder are obtained. M.p.=250-252° C.

NMR $d_6$-DMSO (300 MHz):2.42 ppm:s:3H; 3.70 ppm:s: 3H; 6.71-8.27 ppm:unresolved peak:12H; 9 ppm:s:1H; 11.88 ppm:s:1H.

EXAMPLE 24

Compound 94

[4-(1,6,9-trimethyl-2-oxo-2,9-dihydro-1H-pyrido[2,3-b]indol-3-yl)phenoxy]acetonitrile 0.1 g of Compound 66 (Example 9) is dissolved in 10 ml of DMF. 90 ml of $K_2CO_3$ and then 0.12 ml of bromoacetonitrile are added. The mixture is heated at 90° C. for 48 hours. The reaction medium is poured onto a saturated $NH_4Cl$ solution, the mixture is basified with sodium hydroxide and then extraction is carried out with AcOEt. Purification is carried out by chromatography on a silica column eluted with an AcOEt/petroleum ether (v/v; 75/25) mixture. 20 mg of powder are obtained. M.p.=195-196° C.

NMR $d_6$-DMSO (300 MHz):2.73 ppm:s:3H; 4.27 ppm:s: 6H; 5.02 ppm:s:2H; 7.09-8.26 ppm:unresolved peak:8H.

EXAMPLE 25

Compound 133

1,6-Dimethyl-3-(3-(morpholin-4-ylcarbonyl)phenyl)-1,9-dihydro-2H-pyrido[2,3-b]indol-2-one A) 3-(1,6-Dimethyl-2-oxo-2,9-dihydro-1H-pyrido[2,3-b]indol-3-yl)benzoic acid 200 mg of the compound from Example 18 are dissolved in 10 ml of MeOH. 2 ml of water and then 97 mg of $LiOH.H_2O$ are added. The mixture is heated at 80° C. for 20 hours. It is allowed to return to ambient temperature. The MeOH is evaporated, the residue is taken up in water and then the aqueous phase is washed with AcOEt. The aqueous phase is basified with 5N NaOH and then extracted with AcOEt. The organic phase is dried over $MgSO_4$, filtered and evaporated to dryness. The precipitate obtained is triturated with a petroleum ether/AcOEt (2%) mixture. The precipitate is filtered off and dried. 40 mg of a powder are obtained.

NMR $d_6$-DMSO (300 MHz):2.42 ppm:s:3H; 3.70 ppm:s: 3H; 7.04-8.42 ppm:unresolved peak:8H; 11.93 ppm:s:1H; 12.87 ppm:unresolved peak:1H.

B) 1,6-Dimethyl-3-(3-(morpholin-4-ylcarbonyl)phenyl)-1,9-dihydro-2H-pyrido[2,3-b]indol-2-one 200 mg of the compound from the preceding stage are dissolved in 20 ml of $CH_2Cl_2$. 0.06 ml of morpholine, 340 mg of BOP and 10 ml of DMF are added. The reaction mixture is stirred at ambient temperature for approximately 2 hours. The reaction medium is poured onto saturated $NH_4Cl$ and extracted with AcOEt. Acid/base washing is carried out and then the precipitate obtained is washed with an iPrOH/petroleum ether (v/v; 50/50) mixture. 90 mg of powder are obtained. M.p.=296-298° C.

NMR $d_6$-DMSO (300 MHz):2.42 ppm:s:3H; 3.38-3.62 ppm:s:8H; 3.69 ppm:s:3H; 7.03-8.42 ppm:unresolved peak: 8H; 11.92 ppm:s:1H.

EXAMPLE 26

Compound 123

6-Cyano-3-(3,5-dimethylphenyl)-1-methyl-1,9-dihydro-2H-pyrido[2,3-b]indol-2-one

A) 6-Bromo-3-(3,5-dimethylphenyl)-1-methyl-1,9-dihydro-1H-pyrido[2,3-b]indol-2-one This compound is prepared by the usual methods.

NMR $d_6$-DMSO (300 MHz):2.31 ppm:s:6H; 3.69 ppm:s: 3H; 6.91 ppm:s:1H; 7.28-7.44 ppm:unresolved peak:4H; 8.15 ppm:d:1H; 8.38 ppm:s:1H; 12.30 ppm:s:1H.

B) 6-Cyano-3-(3,5-dimethylphenyl)-1-methyl-1,9-dihydro-2H-pyrido[2,3-b]indol-2-one 2.0 g of the compound from the preceding stage are dissolved in 50 ml of N-methylpyrrolidinone. 0.9 g of CuCN is added and then the mixture is heated at 200° C. for 24 hours. The reaction medium is poured onto $CH_2Cl_2$ and then washing is carried out with a 1N HCl solution. The product is adsorbed on silica and purified by chromatography on a column eluted with an AcOEt/petroleum ether (v/v; 50/50) mixture, then pure AcOEt and then AcOEt/MeOH 2%. 1.2 g of powder are obtained.

NMR $d_6$-DMSO (300 MHz):2.31 ppm:s:6H; 3.70 ppm:s: 3H; 6.93 ppm:s:1H; 7.33 pppm:s:2H; 7.58 ppm:unresolved peak:2H; 8.42 ppm:unresolved peak:2H; 12.55 ppm:s:1H.

EXAMPLE 27

Compound 96

(3-(2,4-Dichlorophenyl)-1,6-dimethyl-2-oxo-1,2-dihydro-9H-pyrido[2,3-b]indol-9-yl)acetonitrile 600 mg of Compound 46 are dissolved in 10 ml of DMF. 42 mg of 95% NaH are added. The mixture is stirred at AT for 30 minutes and then 230 mg of bromoacetonitrile are added. The mixture is stirred at AT for 18 hours. It is concentrated by half and precipitation is carried out by addition of water. 200 mg of the expected product are obtained, M.p.=270° C.

EXAMPLE 28

Compound 92

9-(3-Aminopropyl)-3-(2,4-dichlorophenyl)-1,6-dimethyl-1,6-dimethyl-1,9-dihydro-2H-pyrido[2,3-b]-indol-2-one hydrochloride A) 2-(3-(3-(2,4-Dichlorophenyl)-1,6-dimethyl-2-oxo-1,2-dihydro-9H-pyrido[2,3-b]indol-9-yl)propyl)-1H-isoindole-1,3(2H)-dione 0.5 g of Compound 46 is dissolved in 5 ml of DMF, 107 mg of 95% NaH are added and the mixture is stirred at AT for 10 minutes. 1.25 g of 2-(3-bromo-propyl)-1H-isoindole-1,3 (2H)-dione are added and the mixture is stirred at AT for 18 hours. The mixture is evaporated, the residue is taken up in $CH_2Cl_2$ and the organic phase is washed with NaCl and then $H_2O$. Chromatography is carried out on silica, elution being carried out with $CHCl_3$/MeOH (v/v; 98/2). 160 mg of the expected product are obtained, M.p.=249° C.

B) 9-(3-Aminopropyl)-3-(2,4-dichlorophenyl)-1,6-dimethyl-1,6-dimethyl-1,9-dihydro-2H-pyrido[2,3-b]-indol-2-one chlorohydride 180 mg of the compound from the preceding stage, 3.2 ml of THF, 5 ml of EtOH and 33 μl of hydrazine hydrate are mixed. The mixture is heated at reflux for 18 hours; filtration is carried out and the HCl phase is evaporated. Drying is carried out. 16 mg of the expected product are obtained, M.p.=198° C.

EXAMPLE 29

Compound 91

3-(2,4-Dichlorophenyl)-9-(2-hydroxyethyl)-1,6-dimethyl-1,9-dihydro-2H-pyrido[2,3-b]indol-2-one A) 3-(2,4-Dichlorophenyl)-1,6-dimethyl-9-(2-(tetrahydro-2H-pyran-2-yloxy)ethyl)-1,9-dihydro-2H-pyrido[2,3-b]indol-2-one 695 mg of Compound 46 are dissolved in 7 ml of DMF. 99 mg of 95% NaH are added. The mixture is stirred at AT for 15 minutes. 813 mg of 2-(2-bromoethoxy)tetrahydro-2H-pyran are added and the mixture is stirred at AT for 18 hours. It is evaporated to dryness, the residue is taken up in $CH_2Cl_2$ and the organic phase is washed with NaCl and then $H_2O$. It is dried and evaporated. The residue is chromatographed with $CHCl_3$/MeOH (v/v; 98/2). 390 mg of the expected product are obtained, M.p.=161° C.

B) 3-(2,4-Dichlorophenyl)-9-(2-hydroxyethyl)-1,6-dimethyl-1,9-dihydro-2H-pyrido[2,3-b]indol-2-one 295 mg of the product from the preceding stage, 1.21 mg of p-toluenesulphonic acid and 10 ml of 95% EtOH are mixed. The mixture is heated at reflux for 8 hours and evaporated to dryness. The solid is washed with $NaHCO_3$ and then $H_2O$, and dried. 198 mg of the expected product are obtained, M.p.=240° C.

EXAMPLE 30
Compound 102
3-(2,4-Dimethylphenyl)-1,6,9-trimethyl-1,9-dihydro-2H-pyrido[2,3-b]indol-2-one 400 mg of 3-(2,4-dimethylphenyl)-1,6-dimethyl-1,9-dihydro-2H-pyrido[2,3-b]indol-2-one (compound 101) are dissolved in 10 ml of DMF. 31 mg of 95% NaH are added and the mixture is stirred at AT for 30 minutes. 380 μl of methyl iodide are added and the mixture is stirred at AT for 18 hours. It is evaporated to dryness. The residue is taken up in $CH_2Cl_2$ and the organic phase is washed with NaCl and then water, dried and evaporated. The residue is taken up in $Et_2O$, filtration is carried out and drying is carried out. 300 mg of the expected product are obtained, M.p.=150° C.

EXAMPLE 31
Compound 57
3-(2-Chloro-4-methoxyphenyl)-1,6-dimethyl-1,9-dihydro-2H-pyrido[2,3-b]indol-2-one A mixture of 10 ml of anhydrous DMF and 0.6 ml of anhydrous methanol is prepared and 0.5 g of 60% NaH is added thereto. After gas evolution has ceased, 0.43 g of Compound 59 is added and then the mixture is heated at 80° C. for 24 hours. The reaction medium is poured onto a saturated $NH_4Cl$ solution and then the precipitate formed is filtered off and washed with an isopropanol/petroleum ether (v/v; 50/50) mixture. 0.35 g of the expected compound is obtained.

NMR $d_6$-DMSO (300 MHz):2.46 ppm:s:3H; 3.72 ppm:s:3H; 3.87 ppm:s:3H; 6.98-7.15 ppm:unresolved peak:3H; 7.3-7.6 ppm:unresolved peak:2H; 7.68 ppm:s:1H; 8.15 ppm:s:1H; 11.95 ppm:s:1H.

The chemical structures and the physical properties of a few compounds according to the invention are illustrated in the following table. In this table, Me represents methyl, Et represents ethyl, tBu represents tert-butyl and Bn represents benzyl.

TABLE 4

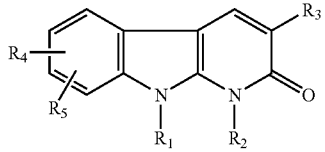
(I)

| Compound | $R_1$ | $R_2$ | $R_3$ | $R_4$, $R_5$ | Characterization M.p.(° C.) or NMR |
|---|---|---|---|---|---|
| 1 | Me | Me | 3,5-diMe-phenyl | 6-Me | 210° C. |
| 2 | Me | Me | 2,4-diCl-phenyl | 6-Me | 170° C. |
| 3 | Me | Me | 3,4-diCl-phenyl | 6-Me | 230° C. |
| 4 | Me | Me | 3-$CF_3$-phenyl | 6-Me | 186° C. |
| 5 | Me | Me | 3,5-di$CF_3$-phenyl | 6-Me | 248° C. |
| 6 | Me | Me | 3,5-diF-phenyl | 6-Me | 240° C. |
| 7 | Me | Me | 3,4,5-triOMe-phenyl | 6-OMe | 224° C. (dec.) |
| 8 | Me | Me | 1,3-benzodioxol-5-yl | 6-OMe | 197° C. |
| 9 | Me | Me | 2,5-diOMe-phenyl | 6-Me | 225° C. |
| 10 | Me | Me | 3,5-diMe-phenyl | 6-Cl | 200° C. |
| 11 | Me | Me | 1,3-benzodioxol-5-yl | 7-OMe | 220° C. (dec.) |
| 12 | Me | Me | 3,4-diOMe-phenyl | 7-OMe | 190° C. |
| 13 | Me | Me | 3,4,5-triOMe-phenyl | 8-OMe | 219° C. |
| 14 | Me | Me | 3,4-diOMe-phenyl | 6-Me | 190° C. |
| 15 | Me | Me | 3,5-diOMe-phenyl | 6-Me | 205° C. |
| 16 | H | Me | 3,5-diMe-phenyl | 6-Me | NMR |
| 17 | Me | Me | 3,5-diOMe-phenyl | 6-Cl | 229 |
| 18 | Me | Me | 3,5-diF-phenyl | H | 232° C. |
| 19 | Me | Me | 2,4-diF-phenyl | 6-Me | 167° C. |
| 20 | Me | Me | 3,5-diF-phenyl | 6-OMe | 189° C. |
| 21 | Me | Me | 2,4-diCl-phenyl | 6-OMe | 130° C. |
| 22 | H | Me | 3,5-diF-phenyl | 6-Me | 189° C. (dec.) |
| 23 | Me | Me | 3,5-diMe-phenyl | 6-OMe | 194° C. |
| 24 | Me | Me | 3-F, 5-$CF_3$-phenyl | 6-Me | 190° C. |
| 25 | Me | Me | 3,5-diF-phenyl | 5-OMe | 238° C. |
| 26 | Me | Me | 1,3-benzodioxol-5-yl | 8-OMe | 197° C. |
| 27 | Me | Me | 3,5-diF-phenyl | 7-OH | 195° C. |
| 28 | Me | Me | 2,4-diCl-phenyl | H | 241° C. |
| 29 | Me | Me | 2,4-diCl-phenyl | 7-OMe | NMR |
| 30 | Me | Me | 2,4-diCl-phenyl | 5-OMe | 228° C. |
| 31 | Me | Me | 2,4-diCl-phenyl | 7-Cl | NMR |
| 32 | Me | Me | 2,4-diCl-phenyl | 5,7-diMe | 240° C. |
| 33 | Me | Me | 2,4-diCl-phenyl | 6-Cl | 258° C. |
| 34 | Me | Me | 3,5-diF-phenyl | 6-Cl | 295° C. |
| 35 | H | Me | 3,5-diF-phenyl | H | 262° C. |
| 36 | H | Me | 2,4-diCl-phenyl | H | NMR |

TABLE 4-continued

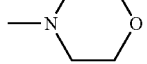

(I)

| Compound | R₁ | R₂ | R₃ | R₄, R₅ | Characterization M.p.(° C.) or NMR |
|---|---|---|---|---|---|
| 37 | Me | Me | 3,5-diMe-phenyl | 6-O(CH₂)₂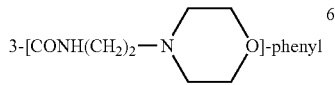 | NMR |
| 38 | Me | Me | 3,5-diCl-phenyl | 6-Me | 268° C. |
| 39 | Me | Me | 2,3-diF-phenyl | 6-Me | 170° C. |
| 40 | Me | Me | 2,3-diF-phenyl | 6-OMe | 179° C. |
| 41 | H | Me | 3-CF₃, 5-F-phenyl | 6-Me | 270° C. |
| 42 | Me | Me | 3-OH-phenyl | 6-Me | NMR |
| 43 | Me | Me | 2-Cl, 4-F-phenyl | 6-Me | 202-203° C. |
| 44 | Me | Me | 4-SO₂Me-phenyl | 6-Me | 245-246° C. |
| 45 | Me | Me | 2-Cl, 4-OMe-phenyl | 6-Me | 196-197° C. |
| 46 | H | Me | 2,4-diCl-phenyl | 6-Me | NMR |
| 47 | Me | Me | 4-OH, 3-tBu-phenyl | 6-Me | NMR |
| 48 | Me | Me | 3-[CONH(CH₂)₂—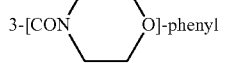O]-phenyl | 6-Me | 194° C. |
| 49 | Me | Me | 3-[CON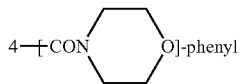O]-phenyl | 6-Me | 252° C. |
| 50 | Me | Me | 3-CH₂NH₂-phenyl | 6-Me | NMR |
| 51 | Me | Me | 3-CONH₂-phenyl | 6-Me | 269° C. |
| 52 | Me | Me | 3-CN-phenyl | 6-Me | 241-242° C. |
| 53 | Me | Me | 4-(CH₂NH₂)-phenyl | 6-Me | 213-214° C. |
| 54 | H | Me | 4-SO₂Me-phenyl | 6-Me | 278° C. |
| 55 | H | Me | 3,4,5-triOMe-phenyl | 6-Me | NMR |
| 56 | H | Me | 4-(CH₂NH₂)-phenyl | 6-Me | 258° C. |
| 57 | H | Me | 2-Cl, 4-OMe-phenyl | 6-Me | NMR |
| 58 | H | Me | 4-CN-phenyl | 6-Me | NMR |
| 59 | H | Me | 2-Cl, 4-F-phenyl | 6-Me | NMR |
| 60 | H | Me | 3-CN-phenyl | 6-Me | 295° C. |
| 61 | H | Me | 3-(CH₂NH₂)-phenyl | 6-Me | NMR |
| 62 | H | Me | 4-COOMe-phenyl | 6-Me | NMR |
| 63 | H | Me | 2-Cl, 4-OH-phenyl | 6-Me | NMR |
| 64 | H | Me | 3-NH₂-phenyl | 6-Me | NMR |
| 65 | H | Me | 4-COOH-phenyl | 6-Me | NMR |
| 66 | Me | Me | 4-OH-phenyl | 6-Me | 280° C. |
| 67 | Me | Me | 4-NMe₂-phenyl | 6-Me | 118° C. |
| 68 | H | Me | 4-OH-phenyl | 6-Me | 186° C. |
| 69 | Me | Me | 2,6-diCl-phenyl | 6-Me | 255° C. |
| 70 | Me | Me | 4-[CONH(CH₂)₂N(CH₃)₂]-phenyl | 6-Me | 105° C. |
| 71 | Me | Me | 4—[CON O]-phenyl | 6-Me | 174° C. |
| 72 | Me | Me | 3-COOMe-phenyl | 6-Me | 172-173° C. |
| 73 | Me | Me | 2-Cl, 4-OH-phenyl | 6-Me | NMR |
| 74 | Me | Me | 2,4-diCl-phenyl | 6-CO₂Me | 270° C. |
| 75 | H | Me | 4-SMe-phenyl | 6-Me | 280° C. |
| 76 | H | Me | 4-N(CH₃)₂-phenyl | 6-Me | 280° C. |
| 77 | H | Me | 3,4-diOMe-phenyl | 6-Me | NMR |
| 78 | CH₂—COO—tBu | Me | 2,4-diCl-phenyl | 6-Me | 113° C. |
| 79 | Me | Me | 2,4-diCl-phenyl | 6-CN | 290° C. |
| 80 | H | Me | 3-CH₂NH(CH₃)-phenyl | 6-Me | NMR |
| 81 | H | Me | 3-CH₂OH-phenyl | 6-Me | NMR |
| 82 | H | Me | 3-Br, 4-OMe-phenyl | 6-Me | NMR |
| 83 | H | Me | 3-(CH=NOH)-phenyl | 6-Me | 290° C. |
| 84 | CH₂—COO—Me | Me | 2,4-diCl-phenyl | 6-Me | 249° C. |

TABLE 4-continued

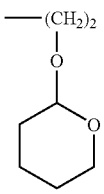

(I)

| Compound | R₁ | R₂ | R₃ | R₄, R₅ | Characterization M.p.(° C.) or NMR |
|---|---|---|---|---|---|
| 85 | CH₂—CONH—Me | Me | 2,4-diCl-phenyl | 6-Me | NMR |
| 86 | Me | Me | 2,4-diCl-phenyl | 6-phenyl | 110° C. |
| 87 | H | Me | 2-Br, 4,5-diOMe-phenyl | 6-Me | NMR |
| 88 | Me | Me | 3-CN-phenyl | 6-CN | >280° C. NMR |
| 89 | Me | Me | 2-Cl, 3,4-diOMe-phenyl | Me | 250° C. |
| 90 | 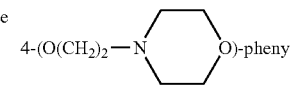 —(CH₂)₂ | Me | 2,4-diCl-phenyl | 6-Me | 161° C. |
| 91 | CH₂CH₂—OH | Me | 2,4-diCl-phenyl | 6-Me | 240° C. |
| 92 | (CH₂)₃—NH₂ | Me | 2,4-diCl-phenyl | 6-Me | 198° C. hydrochloride |
| 93 | Me | Me | 2-Br, 4,5-diOMe-phenyl | 6-Me | 236° C. |
| 94 | Me | Me | 4-(OCH₂CN)-phenyl | 6-Me | 192° C. NMR |
| 95 | Me | Me | 4-(OCH₂CH₂NH₂)-phenyl | 6-Me | 170° C. |
| 96 | CH₂CN | Me | 2,4-diCl-phenyl | 6-Me | 277° C. |
| 97 | CH₂CH₂—NH₂ | Me | 2,4-diCl-phenyl | 6-Me | NMR |
| 98 | H | Me | 2-Cl, 4,5-diOMe-phenyl | 6-Me | NMR |
| 99 | Me | Me | 2-Cl, 4,5-diOMe-phenyl | 6-Me | 245° C. NMR |
| 100 | H | Me | 4-OMe, 3-CN-phenyl | 6-Me | NMR |
| 101 | H | Me | 2,4-diMe-phenyl | 6-Me | NMR |
| 102 | Me | Me | 2,4-diMe-phenyl | 6-Me | 150° C. |
| 103 | H | Me | 3,4-diMe-phenyl | 6-Me | NMR |
| 104 | Me | Me | 3,4-diMe-phenyl | 6-Me | 211° C. |
| 105 | Me | Me | 4-N₃-phenyl | 6-Me | 184° C. |
| 106 | Me | Me | 3,4-diOMe-phenyl | 6-OMe | 160° C. |
| 107 | Me | Me | 4-(O(CH₂)₂—N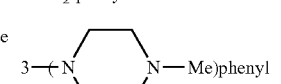O)-phenyl | 6-Me | 180° C. hydrochloride |
| 108 | Me | Me | 2,3-diF-phenyl | 6-OMe | 179° C. |
| 109 | Me | Me | 3-tBu, 4-OMe-phenyl | 6-Me | 231-232° C. |
| 110 | H | Me | 3-COOMe-phenyl | 6-Me | 278-280° C. |
| 111 | H | Me | 4-NH₂-phenyl | 6-Me | NMR |
| 112 | H | Me | 3-(N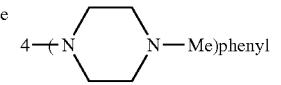N—Me)phenyl | 6-Me | 226° C. |
| 113 | H | Me | 4-(N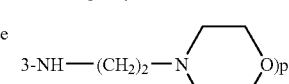N—Me)phenyl | 6-Me | NMR |
| 114 | H | Me | 2,4-diCl-phenyl | 6-Br | 386° C. (dec.) NMR |
| 115 | H | Me | 3-NH—(CH₂)₂—N O)phenyl | 6-Me | 267-269° C. |
| 116 | H | Me | 6-Cl-1,3-benzodioxol-5-yl | 6-Me | NMR |
| 117 | H | Me | 3,5-diOMe-phenyl | 6-Me | 299° C. NMR |
| 118 | H | Me | 3-(NH—CH₂CH₂—NMe₂)-phenyl | 6-Me | 237-239° C. |
| 119 | H | Me | 4-N₃-phenyl | 6-Me | NMR |
| 120 | H | Me | 2,4-diOMe-phenyl | 6-Me | 308-310° C. |
| 121 | H | Me | 3-(NH—C₆H₅)-phenyl | 6-Me | 188-190° C. |
| 122 | H | Me | 3,5-diMe-phenyl | 6-CH₂NH₂ | NMR |
| 123 | H | Me | 3,5-diMe-phenyl | 6-CN | NMR |

TABLE 4-continued

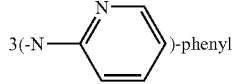

(I)

| Compound | R₁ | R₂ | R₃ | R₄, R₅ | Characterization M.p.(° C.) or NMR |
|---|---|---|---|---|---|
| 124 | Me | Me | 4-NH₂-phenyl | 6-Me | 224° C. NMR |
| 125 | H | Me | 3,5-diMe-phenyl | 6-Br | 320° C. (dec.) NMR |
| 126 | H | Me | 3-CF₃-phenyl | 6-Me | 246° C. NMR |
| 127 | H | Me | 3(-N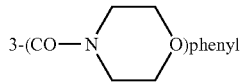)-phenyl | 6-Me | 250° C. |
| 128 | H | Me | 2,4-diCl-phenyl | 6-OMe | 318° C. NMR |
| 129 | H | Me | 3-(OCH₂C₆H₅)-phenyl | 6-Me | 221° C. NMR |
| 130 | H | Me | 3-OH-phenyl | 6-Me | 310° C. (dec.) NMR |
| 131 | H | Me | 3,5-diCl-phenyl | 6-Me | 300-302° C. NMR |
| 132 | H | Me | 3,5-diMe-phenyl | 6-OMe | 317° C. (dec.) |
| 133 | H | Me | 3-(CO—N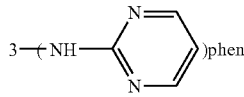O)phenyl | 6-Me | 296-298° C. |
| 134 | H | Me | 4-CONH₂-phenyl | 6-Me | NMR |
| 135 | Me | Me | 3-NH₂-phenyl | 6-Me | 133-135° C. |
| 136 | H | Me | 3,5-diMe-phenyl | 6-CH₂NMe₂ | 238-240° C. |
| 137 | H | Me | 3-(OCH₂COOMe)-phenyl | 6-Me | 208-209° C. |
| 138 | Me | Me | 3-(COMe)-phenyl | 6-Me | 80° C. (dec.) NMR |
| 139 | H | Me | 3—(NH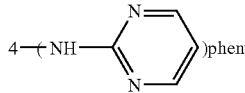)phenyl | 6-Me | 190° C. (dec.) |
| 140 | H | Me | 4—(NH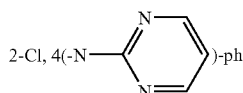)phenyl | 6-Me | 316° C. (dec.) NMR |
| 141 | CH₂CN | Me | 3-(OCH₂CN)-phenyl | 6-Me | 225-227° C. NMR |
| 142 | (CH₂)₂N—(CH₃)₂ | Me | 3-OH-phenyl | 6-Me | 216-218° C. NMR |
| 143 | H | Me | 3-(COMe)phenyl | 6-Me | 258-260° C. |
| 144 | Me | Me | 3-Br, 4-OMe-phenyl | 6-Me | 245-247° C. |
| 145 | H | Me | 3-N₃-phenyl | 6-Me | NMR |
| 146 | Me | Me | 3-N₃-phenyl | 6-Me | 188° C. |
| 147 | H | Me | 2,4-diCN-phenyl | 6-Me | NMR |
| 148 | H | Me | 2-Cl, 4-Br-phenyl | 6-Me | NMR |
| 149 | Me | Me | 2-Cl, 4-Br-phenyl | 6-Me | 251° C. |
| 150 | R₁ + R₂ = —(CH₂)₃— | | 2,4-diCl-phenyl | 6-Me | 197-198° C. NMR |
| 151 | Me | Me | 2,4-diCN-phenyl | 6-Me | 292° C. |
| 152 | H | Me | 2-Cl, 4(-N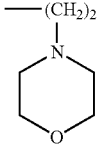)-phenyl | 6-Me | 291° C. |
| 153 | Me | Me | 2,4-diCl-phenyl | 6-Br | 228° C. |
| 154 | —(CH₂)₂—N(morpholine) | Me | 2,4-diCl-phenyl | 6-Br | 179-180° C. (dec.) |
| 155 | CH₂CN | Me | 2,4-diCl-phenyl | 6-COOEt | NMR |
| 156 | H | Me | 2,4-diCl-phenyl | 6-COOEt | NMR |

TABLE 4-continued (I)

| Compound | R₁ | R₂ | R₃ | R₄, R₅ | Characterization M.p.(° C.) or NMR |
|---|---|---|---|---|---|
| 157 | —(CH₂)₂-N(pyrrolidine) | Me | 2,4-diCl-phenyl | 6-Br | 210° C. |
| 158 | H | Me | 2-Cl, 4(-N(piperazine)N—Me)-phenyl | 6-Me | 250° C. (dec.) |
| 159 | H | Me | 2-Cl, 4(-N(pyridine))-phenyl | 6-Me | NMR |
| 160 | H | Me | 2-Cl, 4(-N(morpholine)O)-phenyl | 6-Me | NMR |
| 161 | Me | Me | 2-Cl, 4(-N(Me)(pyrimidine))-phenyl | 6-Me | 262-264° C. |
| 162 | H | Me | 2,4-diCl-phenyl | 6-COOMe | 322-324° C. |
| 163 | H | Me | 2,4-diCl-phenyl | 6-SO₂Me | 338-340° C. |
| 164 | Me | Me | 2,4-diCl-phenyl | 6-SO₂Me | 156-160° C. |
| 165 | H | Me | 2,4-diOMe-phenyl | 6-Br | 207-208° C. |
| 166 | H | Me | 3,5-diCl-phenyl | 6-COOMe | NMR |
| 167 | H | Me | 2-Cl, 4-Br-phenyl | 6-COOMe | 321-323° C. |
| 168 | H | Me | 2-Cl, 4(-N(pyrimidine))phenyl | 6-COOMe | 297-298° C. |
| 169 | H | Me | 2,4-diOMe-phenyl | 6-CN | 239-242° C. |

Compound 16: NMR d₆-DMSO (300 MHz):2.3 ppm:s:6H; 2.4 ppm:s:3H; 3.67 ppm:s:3H; 6.9 ppm:s:1H; 7 ppm:d:1H; 7.3 ppm:unresolved peak:3H; 7.7 ppm:s:1H; 8.26 ppm:s:1H; 11.9 ppm:s:1H.

Compound 29: NMR CDCl₃ (300 MHz):3.93 ppm:s:3H; 4.09 ppm:s:6H; 6.89 ppm:d:1H; 6.92 ppm:dd:1H; 7.3 ppm:dd:1H; 7.38 ppm:d:1H; 7.51 ppm:d:1H; 7.62 ppm:d:1H; 7.94 ppm:s:1H.

Compound 31: NMR d₆-DMSO (300 MHz):4 ppm:s:3H; 4.15 ppm:s:3H; 7.23 ppm:dd:1H; 7.42 ppm:d:1H; 7.47 ppm:dd:1H; 7.68 ppm:d:1H; 7.78 ppm:d:1H; 7.88 ppm:d:1H; 8.23 ppm:s:1H.

Compound 36: NMR CDCl₃ (300 MHz):3.83 ppm:s:3H; 7.29-7.49 ppm:unresolved peak:6H; 7.76 ppm:unresolved peak:1H; 8.03 ppm:s:1H; 8.59 ppm:s:1H.

Compound 37: NMR d₆-DMSO (300 MHz):2.41 ppm:s:6H; 2.63-2.68 ppm:unresolved peak:4H; 2.89 ppm:t (J=5.8):2H; 3.77-3.82 ppm:unresolved peak:4H; 4.08 ppm:unresolved peak:6H; 4.24 ppm:t (J=5.8):2H; 6.95-8.05 ppm:unresolved peak:7H;

Compound 42: NMR d₆-DMSO (200 MHz):2.41 ppm:s:3H; 3.7-4.5 ppm:bs:1H; 3.97 ppm:s:3H; 4.07 ppm:s:3H; 6.65 ppm:d:1H; 7-7.3 ppm: unresolved peak:4H; 7.4 ppm:d:1H; 7.7 ppm:s:1H; 8.25 ppm:s:1H.

Compound 46: NMR d₆-DMSO (300 MHz):2.5 ppm:s:3H; 3.7 ppm:s:3H; 7.1 ppm:d:1H; 7.3-7.5 ppm:unresolved peak: 3H; 7.7 ppm:d:2H; 8.1 ppm:s:1H; 11.9 ppm:s:1H.

Compound 47: NMR CDCl₃ (300 MHz):1.45 ppm:s:9H; 2.5 ppm:s:3H; 4.1 ppm:s:6H; 6.7 ppm:d:1H; 7.2 ppm:d:1H; 7.3 ppm:d:1H; 7.5 ppm:d:1H; 7.6 ppm:d:1H; 8 ppm:s:1H.

Compound 50: NMR CDCl₃ (300 MHz):1.7 ppm:unresolved peak:2H; 2.5 ppm:s:3H; 4.1 ppm:s:6H; 7.1 ppm:d:1H; 7.3 ppm:unresolved peak:2H; 7.4 ppm:t:1H; 7.6 ppm:unresolved peak:2H; 7.7 ppm:s:1H; 8.1 ppm:s:1H.

Compound 55: NMR d$_6$-DMSO (300 MHz):2.43 ppm:s:3H; 3.69 ppm:s:6H; 3.83 ppm:s:6H; 7.03 ppm:d:1H; 7.11 ppm:s: 2H; 7.33 ppm:d:1H; 7.71 ppm:s:1H; 8.37 ppm:s:1H; 11.86 ppm:s:1H.

Compound 58: NMR d$_6$-DMSO (300 MHz):2.43 ppm:s:3H; 3.70 ppm:s:3H; 7.05 ppm:d:1H; 7.3 ppm:d:1H; 7.73 ppm:s: 1H; 7.8 ppm:d:2H; 8.03 ppm:d:2H; 8.54 ppm:s:1H; 12 ppm: s:1H.

Compound 59: NMR d$_6$-DMSO (300 MHz):2.40 ppm:s:3H; 3.67 ppm:s:3H; 7.02-7.06 ppm:unresolved peak:1H; 7.24-7.28 ppm:unresolved peak:1H; 7.34 ppm:d:1H; 7.42-7.47 ppm:unresolved peak:2H; 7.63 ppm:s:1H; 8.1 ppm:s:1H; 11.95 ppm:bs:1H.

Compound 61: NMR d$_6$-DMSO (300 MHz):2.40 ppm:s:3H; 3.25 ppm:s:6H; 7.02 ppm:d:1H; 7.23-7.36 ppm:unresolved peak:3H; 7.61-7.68 ppm:unresolved peak:3H [or 7.05 ppm: d(J=8.1):1H; 7.35 ppm:d(J=8.1):1H; 7.73 ppm:s:1H; 7.78 ppm:unresolved peak:4H]; 8.3 ppm:s:1H.

Compound 62: NMR d$_6$-DMSO (300 MHz):2.43 ppm:s:3H; 3.70 ppm:s:3H; 3.88 ppm:s:3H; 7.05-8.50 ppm:unresolved peak:8H; 11.97 ppm:s:1H.

Compound 63: NMR d$_6$-DMSO (300 MHz):2.41 ppm:s:3H; 3.66 ppm:s:3H; 6.75-9.80 ppm:unresolved peak:8H; 11.87 ppm:s:1H.

Compound 64: NMR d$_6$-DMSO (300 MHz):2.42 ppm:s:3H; 3.67 ppm:s:3H; 4.88 ppm: unresolved peak:2H; 6.47-8.16 ppm:unresolved peak:8H [or 6.49 ppm:d(J=7.5):1H; 6.84 ppm:d(J=7.5):1H; 6.92-7.15 ppm:unresolved peak:3H; 7.34 ppm:d(J=8.1):1H; 7.65 ppm:unresolved peak; 1H; 8.18 ppm: unresolved peak:1H]; 11.82 ppm:unresolved peak:1H.

Compound 65: NMR d$_6$-DMSO (300 MHz):2.43 ppm:s:3H; 3.707 ppm:s:3H; 7.04-8.47 ppm:unresolved peak:8H; 11.95 ppm:s:1H.

Compound 73: NMR d$_6$-DMSO (300 MHz):2.3 ppm:s:3H; 4 ppm:s:3H; 4.1 ppm:s:3H; 6.8 ppm:d:1H; 6.9 ppm:s:1H; 7.2 ppm:d:1H; 7.3 ppm:d:1H; 7.5 ppm:d:1H; 7.7 ppm:s:1H; 8.1 ppm:s:1H; 9.9 ppm: bs:1H.

Compound 77: NMR d$_6$-DMSO (200 MHz):2.4 ppm:s:3H; 3.7 ppm:s:3H; 3.8 ppm:s:6H; 6.9 ppm:d:1H; 7 ppm:d:1H; 7.2-7.3 ppm:unresolved peak:3H; 7.4 ppm:s:1H; 8.3 ppm:s: 1H.

Compound 80: NMR d$_6$-DMSO+TFA (200 MHz):2.4 ppm: s:3H; 2.8 ppm:s:3H; 3.8 ppm:s:3H; 4.3-4.5 ppm:dd:2H; 7.1 ppm:d:1H; 7.3-7.6 ppm:unresolved peak:3H; 7.7 ppm:s:1H; 7.9 ppm:d:1H; 8 ppm:s:1H; 8.4 ppm:s:1H.

Compound 81: NMR d$_6$-DMSO (200 MHz):2.3 ppm:s:3H; 3.6 ppm:s:3H; 4.4 ppm:d:2H; 5.1 ppm:unresolved peak:1H; 7 ppm:d:1H; 7.15-7.3 ppm:unresolved peak:3H; 7.58-7.7 ppm: unresolved peak:3H; 8.2 ppm:s:1H; 11.8-12 ppm:bs:1H.

Compound 82: NMR d$_6$-DMSO (200 MHz):2.4 ppm:s:3H; 3.6 ppm:s:3H; 3.8 ppm:s:3H; 6.95 ppm:d:1H; 7.05 ppm:d: 1H; 7.15 ppm:d:1H; 7.6-7.8 ppm:unresolved peak:2H; 8 ppm:s:1H; 8.3 ppm:s:1H; 11.8 ppm:s:1H.

Compound 85: NMR d$_6$-DMSO (200 MHz):2.3 ppm:s:3H; 2.6 ppm:d:3H; 3.8 ppm:s:3H; 5.2 ppm:s:2H; 7 ppm:d:1H; 7.3 ppm:d:1H; 7.4 ppm:unresolved peak:2H; 7.6 ppm:s:2H; 8.1 ppm:s:1H; 8.4 ppm:d:1H.

Compound 87: NMR d$_6$-DMSO/TFA (200 MHz):2.4 ppm:s: 3H; 3.6 ppm:s:3H; 3.95 ppm:s:3H; 7 ppm:d:1H; 7.15-7.35 ppm:unresolved peak:2H; 7.65 ppm:s:1H; 8.05 ppm:s:1H; 8.1 ppm:s:1H; 8.45 ppm:s:1H.

Compound 88: NMR d$_6$-DMSO/TFA (200 MHz):4.05 ppm: s:3H; 4.25 ppm:s:3H; 7.6-7.9 ppm:unresolved peak:4H; 8.15 ppm:d:1H; 8.25 ppm:s:1H; 8.5 ppm:s:1H; 8.7 ppm:s:1H.

Compound 94: NMR d$_6$-DMSO (300 MHz):2.73 ppm:s:3H; 4.27 ppm:s:6H; 5.02 ppm:s:2H; 7.09-8.26 ppm:unresolved peak:8H.

Compound 97: NMR d$_6$-DMSO/TFA (200 MHz):2.4 ppm:s: 3H; 2.95 ppm:t:2H; 4 ppm:s:3H; 4.6 ppm:t:2H; 7.2 ppm:d: 1H; 7.4-7.7 ppm:unresolved peak:3H; 7.75 ppm:s:2H; 8.2 ppm:s:1H.

Compound 98: NMR d$_6$-DMSO/TFA (200 MHz):2.4 ppm:s: 3H; 3.6 ppm:s:3H; 3.7 ppm:s:3H; 3.8 ppm:s:3H; 6.95 ppm: s:1H; 7-7.1 ppm:unresolved peak:2H; 7.35 ppm:d:1H; 7.6 ppm:s:1H; 8.05 ppm:s:1H.

Compound 99: NMR d$_6$-DMSO/TFA (200 MHz):2.3 ppm:s: 3H; 3.7 ppm:s:3H; 3.75 ppm:s:3H; 3.9 ppm:s:3H; 4.05 ppm: s:3H; 6.85 ppm:s:1H; 7 ppm:s:1H; 7.05 ppm:s:1H; 7.4 ppm: d:1H; 7.6 ppm:s:1H; 8 ppm:s:1H.

Compound 100: NMR d$_6$-DMSO/TFA (200 MHz):2.4 ppm: s:3H; 3.65 ppm:s:3H; 3.7 ppm:s:3H; 3.8 ppm:s:3H; 6.95 ppm:s:1H; 7.05 ppm:d:1H; 7.2 ppm:s:1H; 7.35 ppm:d:1H; 7.65 ppm:s:1H; 8.05 ppm:s:1H.

Compound 101: NMR d$_6$-DMSO/TFA (200 MHz):2.2 ppm: s:3H; 2.3 ppm:s:3H; 2.4 ppm:s:3H; 3.75 ppm:s:3H; 7-7.2 ppm:unresolved peak:4H; 7.4 ppm:d:1H; 7.7 ppm:s:1H; 8 ppm:s:1H.

Compound 103: NMR d$_6$-DMSO/TFA (200 MHz):2.3 ppm: s:3H; 2.45 ppm:s:3H; 2.5 ppm:s:3H; 3.7 ppm:s:3H; 7.1 ppm: d:1H; 7.2 ppm:d:1H; 7.4 ppm:d:1H; 7.5 ppm:d:1H; 7.6 ppm: s:1H; 7.75 ppm:s:1H; 8.35 ppm:s:1H.

Compound 112: NMR d$_6$-DMSO (300 MHz):2.41 ppm:s:3H; 2.46 ppm:s:3H; 2.69-2.72 ppm:unresolved peak:4H; 3.19-3.28 ppm:unresolved peak:4H; 3.76 ppm:s:3H; 6.93 ppm:dd: 1H; 7.09 ppm:d:1H; 7.15 ppm:d:1H; 7.28 ppm:d:1H; 7.33 ppm:unresolved peak:2H; 7.61 ppm:s:1H; 8.19 ppm:s:1H.

Compound 114: NMR d$_6$-DMSO (300 MHz):3.69 ppm:s:3H; 7.4 ppm:unresolved peak:4H; 7.67 ppm:d:1H; 8.09 ppm:d: 1H; 8.29 ppm:s:1H; 12.28 ppm:s:1H.

Compound 116: NMR d$_6$-DMSO (300 MHz):2.41 ppm:s:3H; 3.67 ppm:s:3H; 6.12 ppm:s:2H; 7.02 ppm:s:1H; 7.10 ppm:s: 1H; 7.19 ppm:s:1H; 7.36 ppm:d:1H; 7.63 ppm:s:1H; 8.05 ppm:s:1H; 11.92 ppm:s:1H.

Compound 117: NMR d$_6$-DMSO (300 MHz):2.42 ppm:s:3H; 3.68 ppm:s:3H; 3.78 ppm:s:6H; 6.41-8.37 ppm:unresolved peak:7H; 11.89 ppm:s:1H.

Compound 119: NMR d$_6$-DMSO (200 MHz):2.4 ppm:s:3H; 3.7 ppm:s:3H; 7-7.2 ppm:unresolved peak:3H; 7.4 ppm:d: 1H; 7.7 ppm:s:1H; 7.8 ppm:d:2H; 8.4 ppm:s:1H.

Compound 122: NMR d$_6$-DMSO (300 MHz):2.50 ppm:s:6H; 3.79 ppm:s:3H; 4.03 ppm:unresolved peak:2H; 6.92-8.28 ppm:unresolved peak:7H; 12.46 ppm:s:1H.

Compound 124: NMR d$_6$-DMSO (300 MHz):2.43 ppm:s:3H; 3.98 ppm:s:3H; 4.08 ppm:s:3H; 7.06-7.16 ppm:unresolved peak:8H.

Compound 125: NMR d$_6$-DMSO (300 MHz):2.31 ppm:s:6H; 3.69 ppm:s:3H; 6.91 ppm:s:1H; 7.28-7.44 ppm:unresolved peak:4H; 8.15 ppm:d:1H; 8.38 ppm:s:1H; 12.30 ppm:s:1H.

Compound 126: NMR d$_6$-DMSO (300 MHz):2.43 ppm:s:3H; 3.70 ppm:s:3H; 7.05-8.88 ppm:unresolved peak:8H; 11.97 ppm:s:1H.

Compound 128: NMR d$_6$-DMSO (300 MHz):3.61 ppm:s:3H; 3.78 ppm:s:3H; 6.83 ppm:dd:1H; 7.33-7.48 ppm:unresolved peak:4H; 7.66 ppm:d:1H; 8.17 ppm:s:1H; 11.91 ppm:s:1H.

Compound 129: NMR d$_6$-DMSO (300 MHz):2.42 ppm:s:3H; 3.69 ppm:s:3H; 5.15 ppm:s:2H; 6.93-8.36 ppm:unresolved peak:13H; 11.88 ppm:s:1H.

Compound 130: NMR d$_6$-DMSO (300 MHz):2.42 ppm:s:3H; 3.68 ppm:s:3H; 6.67 ppm:dd:1H; 7.02 ppm:dd:1H; 7.03-7.24 ppm:unresolved peak:3H; 7.34 ppm:d:1H; 7.68 ppm:s:1H; 8.25 ppm:s:1H; 9.26 ppm:bs:1H; 11.85 ppm:bs:1H.

Compound 131: NMR d$_6$-DMSO (300 MHz):2.43 ppm:s:3H; 7.05-8.61 ppm:unresolved peak:7H; 12.00 ppm:s:1H.

Compound 134: NMR d$_6$-DMSO (300 MHz):2.43 ppm:s:3H; 4.02 ppm:s:3H; 7.06 ppm:dd:1H; 7.29 ppm:bs:1H; 7.35 ppm:d:1H; 7.72 ppm:s:1H; 7.84-7.94 ppm:unresolved peak:5H; 8.45 ppm:s:1H.

Compound 138: NMR d$_6$-DMSO (300 MHz):1.71 ppm:s:3H; 2.44 ppm:s:3H; 2.64 ppm:s:3H; 4.02 ppm:s:3H; 4.20 ppm:s:3H; 7.12 ppm:d:1H; 7.48-7.56 ppm:unresolved peak:2H; 7.76 ppm:unresolved peak:1H; 7.87 ppm:d:1H; 8.03 ppm:d:1H; 8.35 ppm:unresolved peak:1H; 8.46 ppm:s:1H.

Compound 140: NMR d$_6$-DMSO (300 MHz):2.79 ppm:s:3H; 3.69 ppm:s:3H; 6.83 ppm:t:1H; 7.03 ppm:dd:1H; 7.34 ppm:d:1H; 7.66-7.80 ppm:unresolved peak:5H; 8.27 ppm:s:1H; 8.49 ppm:d:1H; 9.63 ppm:s:1H; 11.84 ppm:s:1H.

Compound 141: NMR d$_6$-DMSO (300 MHz):2.45 ppm:s:3H; 4.04 ppm:s:3H; 5.22 ppm:s:2H; 5.87 ppm:s:2H; 7.01-9.31 ppm:unresolved peak:8H.

Compound 142: NMR d$_6$-DMSO (300 MHz):2.21 ppm:s:6H; 2.43 ppm:s:3H; 2.64 ppm:t:2H; 3.99 ppm:s:3H; 4.62 ppm:t:2H; 6.67-8.29 ppm:unresolved peak:8H; 9.27 ppm:s:1H.

Compound 145: NMR d$_6$-DMSO/TFA (200 MHz):2.4 ppm:s:3H; 3.7 ppm:s:3H; 6.9-7.1 ppm:unresolved peak:2H; 7.3-7.45 ppm:unresolved peak:3H; 7.5-7.7 ppm:unresolved peak:2H; 8.35 ppm:s:1H.

Compound 148: NMR d$_6$-DMSO (300 MHz):2.40 ppm:s:3H; 3.67 ppm:s:3H; 7.04 ppm:d:1H; 7.35 ppm:unresolved peak:2H; 7.57 ppm:dd:1H; 7.63 ppm:s:1H; 7.77 ppm:d:1H; 8.12 ppm:s:1H; 11.96 ppm:s:1H.

Compound 150: NMR d$_6$-DMSO (300 MHz):2.43 ppm:unresolved peak:2H; 2.51 ppm:s:3H; 4.10-4.30 ppm:unresolved peak:4H; 7.17-8.20 ppm:unresolved peak:7H.

Compound 155: NMR d$_6$-DMSO (300 MHz):1.36 ppm:t (J=7.0): 3H; 4.02 ppm:s:3H; 4.34 ppm:q(J=7.0):2H; 5.97 ppm:s:2H; 7.48 ppm:unresolved peak:2H; 7.70 ppm:s:1H; 7.88 ppm:d(J=8.6):1H; 7.98 ppm:dd (J=1.5; J=8.6):1H; 8.47 ppm:s:1H; 8.61 ppm:s:1H.

Compound 156: NMR d$_6$-DMSO (300 MHz):1.33 ppm:t (J=7):3H; 3.70 ppm:s:3H; 4.32 ppm:q(J=7):2H; 7.41 ppm:unresolved peak:2H; 7.46 ppm: d(J=8.5):1H; 7.67 ppm:s:1H; 7.86 ppm:d (J=8.5):1H; 8.34 ppm:s:1H; 8.53 ppm:s:1H; 12.46 ppm:s:1H.

Compound 159: NMR d$_6$-DMSO (300 MHz):2.42 ppm:s:3H; 3.69 ppm:s:3H; 7.05 ppm:d (J=7.0):1H; 7.21 ppm:d (J=7.29): 1H; 7.37 ppm:d(J=8.15):2H; 7.51 ppm:d (J=2.6):1H; 7.54 ppm:s:1H; 7.64 ppm:s:1H; 8.14 ppm:s:1H; 8.34 ppm: d(J=7.22):2H; 10.71 ppm:s:1H; 12.03 ppm:s:1H.

Compound 160: NMR d$_6$-DMSO (300 MHz):2.40 ppm:s:3H; 3.17 ppm:unresolved peak:4H; 3.66 ppm:s:3H; 3.75 ppm: unresolved peak:4H; 6.94 ppm:dd(J=2.45; J=8.60):1H; 7.03 ppm:unresolved peak:2H; 7.23 ppm:d(J=8.51):1H; 7.34 ppm:d(J=8.12):1H; 7.62 ppm:s:1H; 8.02 ppm:s:1H; 11.87 ppm:s:1H.

Compound 166 d$_6$-DMSO:3.73 ppm:s:3H; 3.97 ppm:s:3H; 7.56 ppm:d:1H; 7.63 ppm:d:1H; 7.95 ppm:d:1H; 8.07 ppm: unresolved peak:2H; 8.73 ppm:s:1H; 8.92 ppm:s:1H; 12.57 ppm:s:1H.

The compounds according to the invention have formed the subject of pharmacological trials which make it possible to determine their anticancer activity.

The compounds of formula (I) according to the present invention were tested in vitro on a human breast cancer cell line: the MDA-MB-231 line available from the American Type Culture Collection (reference HTB26).

The antiproliferative effect is evaluated according to J. M. Derocq et al., FEBS Letters, 1998, 425, 419-425: the level of incorporation of [$^3$H]thymidine in the DNA of the treated cells is measured after incubating a compound of formula (I) for 96 hours. The inhibitory concentration 50 (IC$_{50}$) is defined as the concentration which inhibits cell proliferation by 50%.

The compounds according to the invention exhibit an IC$_{50}$ generally of less than 10 μM with regard to the MDA-MB-231 line.

The compounds of formula (I) were also tested on another human breast cancer cell line, a "multi-drug-resistant" (MDR) line referred to as MDA-A$_1$. This line is described by E. Collomb, C. Dussert and P. M. Martin in Cytometry, 1991, 12(1), 15-25.

The term "multi-resistant" which describes this line means that the said line is generally not very sensitive to the chemotherapeutic drugs commonly used and in particular to antimitotics of natural origin, such as paclitaxel, vincristine or vinblastine.

The compounds according to the invention exhibit an IC$_{50}$ generally of less than 10 μM with regard to the MDA-A$_1$ multi-resistant line.

The compounds according to the invention were also tested in vivo in murine models of human tumour xenografts according to the methods described in the literature: Mooberry S. L. et al., Int. J. Cancer, 2003, 104 (4), 512-521; Polin L. et al., Invest. New Drugs, 2002, 20 (1), 13-22; Corbett T. H et al., Invest. New Drugs, 1999, 17 (1), 17-27. Fragments of human tumours with a diameter of 2 to 3 mm are implanted subcutaneously in SCID (Severe Combined Immunodeficiency) mice of the Balb/C strain (Iffa-Credo, Lyons, France). When these tumours reach a weight of 50-60 mg, the compounds are administered orally or intravenously every day or every two days throughout the duration of the experiment (20 to 40 days) at doses varying from 10 to 300 mg/kg per administration. The weight of the tumours is estimated according to the formula: W (weight of the tumour in mg)=(a×b$^2$)/2, where a and b respectively represent the length and the width in mm of the tumour implant. The measurement of a and of b is carried out using a calliper rule. The antitumour effectiveness is evaluated by comparing the mean weight of the tumours in the group of animals treated with the test compound (T) with that of the animals of the control group to which only the solvent of the compound has been administered (C). This measurement, expressed as % of the ratio T/C, is carried out when C reaches approximately 1 000 mg. The compounds according to the invention demonstrated an in vivo antitumour activity (ratio T/C of less than 100%), some very significantly with a ratio T/C of less than or equal to 42%.

Thus, according to the present invention, it is apparent that the compounds of formula (I) inhibit the proliferation of tumour cells, including those of cells exhibiting multi-resistance. It is thus apparent that the compounds according to the invention have an anticancer activity.

Thus, according to another of its aspects, a subject-matter of the invention is medicaments which comprise a compound of formula (I) or an addition salt of the latter with a pharmaceutically acceptable acid or also a hydrate or a solvate of the compound of formula (I).

These medicaments find their use in therapeutics, in particular in the treatment of or protection from diseases caused or exacerbated by the proliferation of tumour cells.

These compounds, as inhibitor of the proliferation of tumour cells, are of use in the treatment of solid tumours, both primary and metastatic solid tumours, carcinomas and cancers, in particular: breast cancer; lung cancer; cancer of the small intestine, cancer of the colon and of the rectum; cancer of the respiratory tract, of the oropharynx and of the hypopharynx; cancer of the oesophagus; liver cancer, stomach cancer, cancer of the bile ducts, cancer of the gall bladder, cancer of the pancreas; cancers of the urinary tract, including kidney, urothelium and bladder; cancers of the female genital tract, including cancer of the uterus, cervix and ovaries, choriocarcinoma and trophoblastic cancer; cancers of the male genital tract, including cancer of the prostate, seminal vesicles and testicles, tumours of the germinal cells; cancers of the endocrine glands, including cancer of the thyroid, pituitary gland and adrenal glands; skin cancers, including haemangiomas, melanomas and sarcomas, including Kaposi's sarcoma; tumours of the brain, nerves, eyes and meninges, including astrocytomas, gliomas, glioblastomas, retinoblastomas, neurinomas, neuroblastomas, schwannomas and meningiomas; solid tumours resulting from haematopoietic malignant tumours, including leukaemias, chloromas, plasmacytomas, fungoid mycosis, T-cell lymphoma or leukaemia, non-Hodgkin's lymphoma, malignant haemopathies and myelomas.

According to another of its aspects, the present invention relates to pharmaceutical compositions comprising, as active principle, a compound according to the invention. These pharmaceutical compositions comprise an effective dose of at least one compound according to the invention, or a pharmaceutically acceptable salt, a hydrate or solvate of the said compound, and at least one pharmaceutically acceptable excipient.

The said excipients are chosen, according to the pharmaceutical form and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its optional salt, solvate or hydrate, can be administered in unit administration form, as a mixture with conventional pharmaceutical excipients, to animals and man for the prophylaxis or treatment of the above disorders or diseases.

The appropriate unit administration forms comprise forms by the oral route, such as tablets, soft or hard gelatin capsules, powders, granules and oral solutions or suspensions, sublingual, buccal, intratracheal, intraocular or intranasal, by inhalation, administration forms, topical, transdermal, subcutaneous, intramuscular or intravenous administration forms, rectal administration forms and implants. Use may be made, for the topical application, of the compounds according to the invention in creams, gels, ointments or lotions.

The compounds of formula (I) above can be used at daily doses of 0.002 to 2 000 mg per kilogram of body weight of the mammal to be treated, preferably at daily doses of 0.1 to 300 mg/kg. In man, the dose can preferably vary from 0.02 to 10 000 mg per day, more particularly from 1 to 3 000 mg, depending on the age of the subject to be treated or the type of treatment: prophylactic or curative.

There may be specific cases where higher or lower dosages are appropriate; such dosages do not depart from the scope of the invention. According to usual practice, the dosage appropriate to each patient is determined by the doctor according to the method of administration and the weight and response of the said patient.

The present invention, according to another of its aspects, also relates to a method for the treatment of the pathologies indicated above which comprises the administration, to a patient, of an effective dose of a compound according to the invention, or one of its pharmaceutically acceptable salts or its hydrates or solvates.

According to the present invention, the compound or compounds of formula (I) can be administered in combination with one (or more) anticancer active principle(s), in particular antitumour compounds, such as alkylating agents, such as alkylsulphonates (busulfan), dacarbazine, procarbazine, nitrogen mustards (chlormethine, melphalan, chlorambucil), cyclophosphamide or ifosfamide; nitrosoureas, such as carmustine, lomustine, semustine or streptozocin; antineoplastic alkaloids, such as vincristine or vinblastine; taxanes, such as paclitaxel or taxotere; antineoplastic antibiotics, such as actinomycin; intercalating agents, antineoplastic antimetabolites, folate antagonists or methotrexate; purine synthesis inhibitors; purine analogues, such as mercaptopurine or 6-thioguanine; pyrimidine synthesis inhibitors, aromatase inhibitors, capecitabine or pyrimidine analogues, such as fluorouracil, gemcitabine, cytarabine and cytosine arabinoside; brequinar; topoisomerase inhibitors, such as camptothecin or etoposide; anticancer hormonal agonists and antagonists, including tamoxifen; kinase inhibitors, imatinib; growth factor inhibitors; antiinflammatories, such as pentosan polysulphate, corticosteroids, prednisone or dexamethasone; antitopoisomerases, such as etoposide, anthracyclines, including doxorubicin, bleomycin, mitomycin and mithramycin; anticancer metal complexes, platinum complexes, cisplatin, carboplatin or oxaliplatin; interferon-alpha, triphenyl thiophosphoramide or altretamine; antiangiogenic agents; thalidomide; immunotherapy adjuvants; or vaccines.

I claim:

1. A compound corresponding to the formula (I):

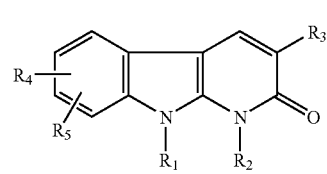

in which:

$R_1$ represents a hydrogen atom, a $(C_1-C_4)$alkyl group or a $(CH_2)_n$OH, $(CH_2)_n$—O-tetrahydropyran-2-yl, $(CH_2)_n$NR'$_6$R'$_7$, $(CH_2)_n$CN, $(CH_2)_n$CO$_2$(C$_1$-C$_4$)alk or $(CH_2)_n$CONR$_6$R$_7$ group;

$R_2$ represents a hydrogen atom or a $(C_1-C_4)$alkyl group;

$R_3$ represents a phenyl monosubstituted by a hydroxyl, hydroxymethyl, carboxyl, $(C_1-C_4)$alkanoyl, azido, $(C_1-C_4)$-alkoxycarbonyl, hydroxyiminomethyl, $(C_1-C_4)$ alkylsulphonyl, trifluoromethyl, thiol, $(C_1-C_4)$alkylthio, cyano, $(CH_2)_m NR'_7 R_{10}$, $CONR_6 R_8$ or $O(CH_2)_n R_9$ group; a phenyl substituted by 2 to 5 identical or different substituents chosen from trifluoromethyl, hydroxyl, hydroxymethyl, carboxyl, $(C_1-C_4)$alkanoyl, azido, $(C_1-C_4)$alkoxycarbonyl, hydroxyiminomethyl, thiol, $(C_1-C_4)$alkylthio, $(C_1-C_4)$alkylsulphonyl, phenyl, cyano, $(CH_2)_m NR'_7 R_{10}$, $CONR_6 R_8$ or $O(CH_2)_n R_9$ group; or $R_3$ represents a benzodioxolyl group which is unsubstituted or substituted on the phenyl by a halogen atom;

$R_4$ and $R_5$ are identical or different and each independently represent a hydrogen or halogen atom or a hydroxyl, $(C_1-C_4)$alkyl, trifluoromethyl, phenyl, cyano, $(C_1-C_4)$ alkoxy, $(C_1-C_4)$alkoxycarbonyl, $(C_1-C_4)$alkylsulphonyl, $O—(CH_2)_n NR_6 R_7$ or $(CH_2)_n NR_6 R_7$ group;

$R_6$ represents hydrogen or a $(C_1-C_4)$alkyl group;

$R_7$ represents hydrogen or a $(C_1-C_4)$alkyl group;

or $R_6$ and $R_7$, together with the nitrogen atom to which they are bonded, form a heterocyclic radical chosen from: piperidyl, morpholinyl, pyrrolidinyl, piperazinyl or 4-methylpiperazin-1-yl;

$R'_6$ represents hydrogen or a $(C_1-C_4)$alkyl group;

$R'_7$ represents hydrogen or a $(C_1-C_4)$alkyl group;

or $R'_6$ and $R'_7$, together with the nitrogen atom to which they are bonded, form a heterocyclic radical chosen from morpholinyl or pyrrolidinyl;

$R_8$ represents hydrogen, a $(C_1-C_4)$alkyl group or a $—(CH_2)_n NR_6 R_7$ group;

or $R_6$ and $R_8$, together with the nitrogen atom to which they are bonded, form a heterocyclic radical chosen from: piperidyl, morpholinyl, pyrrolidinyl, piperazinyl or 4-methylpiperazin-1-yl;

$R_9$ represents a phenyl radical or an amino, morpholin-4-yl, cyano or $(C_1-C_4)$alkoxycarbonyl group;

$R_{10}$ represents $R'_6$ or a phenyl, pyridyl, pyrimidinyl or a $(CH_2)_n NR'_6 R'_7$ group;

or $R'_7$ and $R_{10}$, together with the nitrogen atom to which they are bonded, form a heterocyclic radical chosen from piperazinyl or 4-methylpiperazin-1-yl;

n represents 1, 2 or 3;

m represents 0 or 1;

Alk represents an alkyl;

or an acid addition salt thereof.

2. A compound of formula (I) according to claim 1, wherein:

$R_1$ represents a hydrogen atom or a methyl, cyanomethyl, $(C_1-C_4)$alkoxycarbonylmethyl, aminomethyl, aminoethyl, aminopropyl or pyrrolidinoethyl group;

and/or $R_2$ represents a methyl group;

and/or $R_3$ represents a phenyl monosubstituted by a hydroxyl, $(C_1-C_4)$alkoxycarbonyl, methylsulphonyl, trifluoromethyl, methylthio, cyanomethoxy, aminoethoxy, acetyl, hydroxymethyl, cyano, amino, azido, aminomethyl, hydroxyiminomethyl, or a $(CH_2)_m NR'_7 R_{10}$ group in which $R'_7$ represents a hydrogen atom or a methyl, $R_{10}$ represents a hydrogen atom or a phenyl, pyridyl or pyrimidinyl group or $R'_7$ and $R_{10}$, together with the nitrogen atom to which they are bonded, form a piperazin-1-yl or 4-methylpiperazin-1-yl group, and m represents zero or one; or $R_3$ represents a phenyl substituted by 2 to 3 identical or different substituents chosen from a methylthio, trifluoromethyl, hydroxyl, $(C_1-C_4)$ alkoxycarbonyl, methylsulphonyl, cyanomethoxy, aminoethoxy, acetyl, hydroxymethyl, cyano, amino, aminomethyl, hydroxyiminomethyl, or a $(CH_2)_m NR'_7 R_{10}$ group in which $R'_7$ represents a hydrogen atom or a methyl, $R_{10}$ represents a hydrogen atom or a phenyl, pyridyl or pyrimidinyl group or $R'_7$ and $R_{10}$, together with the nitrogen atom to which they are bonded, form a piperazin-1-yl or 4-methylpiperazin-1-yl group, and m represents zero or one; or $R_3$ represents a benzodioxolyl group which is unsubstituted or substituted on the phenyl by a halogen atom;

and/or $R_4$ represents a halogen atom or a methyl, methoxy or $(C_1-C_4)$alkoxycarbonyl group;

and/or $R_5$ represents a hydrogen atom or a methyl group; or an acid addition salt thereof.

3. A compound chosen from:

3-(2,4-dimethoxyphenyl)-1,9-dimethyl-2-oxo-2,9-dihydro-1H-pyrido[2,3-b]indole-6-carboxylic acid;

3-(2,4-dimethoxyphenyl)-1,6-dimethyl-1,9-dihydro-2H-pyrido[2,3-b]indol-2-one;

3-(3-hydroxymethylphenyl)-1,6-dimethyl-1,9-dihydro-2H-pyrido[2,3-b]indol-2-one;

3-(2,4-dichlorophenyl)-1,6-dimethyl-1,9-dihydro-2H-pyrido[2,3-b]indol-2-one;

3-(1,6-dimethyl-2-oxo-2,9-dihydro-1H-pyrido[2,3-b]-indol-3-yl)benzonitrile;

3-(4-aminophenyl)-1,6-dimethyl-1,9-dihydro-2H-pyrido [2,3-b]indol-2-one;

3-(6-chloro-1,3-benzodioxol-5-yl)-1,6-dimethyl-1,9-dihydro-2H-pyrido[2,3-b]indol-2-one;

1,6-dimethyl-1,9-dihydro-3-(phenylaminophenyl)-2H-pyrido[2,3-b]indol-2-one;

6-bromo-3-(3,5-dimethylphenyl)-1-methyl-1,9-dihydro-2H-pyrido[2,3-b]indol-2-one;

1,6-dimethyl-3-(3-(trifluoromethyl)phenyl)-1,9-dihydro-2H-pyrido[2,3-b]indol-2-one;

1,6-dimethyl-3-(3-(pyridin-2-ylamino)phenyl)-1,9-dihydro-2H-pyrido[2,3-b]indol-2-one;

1,6-dimethyl-3-(3-(pyrimidin-2-ylamino)phenyl)-1,9-dihydro-2H-pyrido[2,3-b]indol-2-one;

3-(3-acetylphenyl)-1,6-dimethyl-1,9-dihydro-2H-pyrido [2,3-b]indol-2-one;

methyl 9-(cyanomethyl)-3-(2,4-dichlorophenyl)-2-oxo-2, 9-dihydro-1H-pyrido[2,3-b]indole-6-carboxylate;

or an acid addition salt thereof.

4. A pharmaceutical composition comprising a compound of formula (I) according to claim 1, or a pharmaceutically acceptable salt thereof, and at least one pharmaceutically acceptable excipient.

5. A pharmaceutical composition comprising a compound of formula (I) according to claim 2, or a pharmaceutically acceptable salt thereof, and at least one pharmaceutically acceptable excipient.

6. A pharmaceutical composition comprising a compound of formula (I) according to claim 3, or a pharmaceutically acceptable salt thereof, and at least one pharmaceutically acceptable excipient.

7. The compound according to claim 3, which is 3-(2,4-dimethoxyphenyl)-1,9-dimethyl-2-oxo-2,9-dihydro-1H-pyrido[2,3-b]indole-6-carboxylic acid or an acid addition salt thereof.

8. The compound according to claim 3, which is 3-(2,4-dichlorophenyl)-1,6-dimethyl-1,9-dihydro-2H-pyrido[2,3-b]indol-2-one or an acid addition salt thereof.

9. The compound according to claim 3, which is 1,6-dimethyl-3-(3-(pyridin-2-ylamino)phenyl)-1,9-dihydro-2H-pyrido[2,3-b]indol-2-one or an acid addition salt thereof.

10. The compound according to claim 3, which is 1,6-dimethyl-3-(3-(pyrimidin-2-ylamino)phenyl)-1,9-dihydro-2H-pyrido[2,3-b]indol-2-one or an acid addition salt thereof.

* * * * *